US011903715B1

United States Patent
Deka et al.

(10) Patent No.: US 11,903,715 B1
(45) Date of Patent: Feb. 20, 2024

(54) SYSTEM AND METHOD FOR A WEARABLE BIOLOGICAL FIELD SENSING DEVICE USING FERROMAGNETIC RESONANCE

(71) Applicant: Sonera Magnetics, Inc., Berkeley, CA (US)

(72) Inventors: Nishita Deka, Berkeley, CA (US); Dominic Labanowski, Berkeley, CA (US)

(73) Assignee: Sonera Magnetics, Inc., Berkeley, CA (US)

(*) Notice: Subject to any disclaimer, the term of this patent is extended or adjusted under 35 U.S.C. 154(b) by 267 days.

(21) Appl. No.: 17/161,385

(22) Filed: Jan. 28, 2021

Related U.S. Application Data

(60) Provisional application No. 63/093,700, filed on Oct. 19, 2020, provisional application No. 62/966,682, filed on Jan. 28, 2020.

(51) Int. Cl.
*A61B 5/245* (2021.01)
*A61B 5/00* (2006.01)

(52) U.S. Cl.
CPC ............ *A61B 5/245* (2021.01); *A61B 5/6803* (2013.01); *A61B 2560/0209* (2013.01);
(Continued)

(58) Field of Classification Search
CPC ....... A61B 5/245; A61B 5/6803; A61B 5/242; A61B 5/248; A61B 2560/0209;
(Continued)

(56) References Cited

U.S. PATENT DOCUMENTS

| 4,078,186 A | 3/1978 | Folen et al. |
| 4,951,674 A * | 8/1990 | Zanakis ................. A61B 5/242 600/409 |

(Continued)

FOREIGN PATENT DOCUMENTS

| WO | 2018111769 A1 | 6/2018 | |
| WO | WO-2018111769 A1 * | 6/2018 | ............... B06B 1/06 |

OTHER PUBLICATIONS

Huang Liang et al: "Theoretical investigation of magnetoelectric surface acoustic wave characteristics of ZnO/Metglas layered composite", AIP Advances, American Institute of Physics, 2 Huntington Quadrangle, Melville, NY 11747, vol. 6, No. 1, Jan. 8, 2016 (Jan. 8, 2016), XP012203752, DOI: 10.1063/1.4939846 [retrieved on Jan. 1, 1901] *sections I. and IV.; figure 1*.

(Continued)

*Primary Examiner* — Sean D Mattson
(74) *Attorney, Agent, or Firm* — Alpine Patents LLC; Brian Van Osdol

(57) ABSTRACT

A system and method for a wearable field sensing device for biological electromagnetic (EM) field measurement including: a wearable structure; a biological sensor array, on or within the wearable structure, such that each biological sensor is situated adjacent to the body of the user, and wherein each biological sensor includes at least one ferromagnetic resonance (FMR) sensor; a power system, providing the power for the system; and control circuitry, electrically coupled to the system. The FMR sensor comprises an acoustically driven ferromagnetic resonance (ADFMR) sensor. The system may additionally include sensor shielding and an ambient sensor array to detect a block external fields.

20 Claims, 30 Drawing Sheets

Side View

Interior View

(52) U.S. Cl.
CPC .............. *A61B 2560/0214* (2013.01); *A61B 2560/0242* (2013.01); *A61B 2562/0223* (2013.01); *A61B 2562/046* (2013.01); *A61B 2562/182* (2013.01)

(58) Field of Classification Search
CPC .... A61B 2560/0214; A61B 2560/0242; A61B 2562/046; A61B 2562/182; A61B 2562/0223; G01R 33/32–326
See application file for complete search history.

(56) References Cited

U.S. PATENT DOCUMENTS

| | | | |
|---|---|---|---|
| 6,046,657 | A | 4/2000 | Alers et al. |
| 6,279,406 | B1 | 8/2001 | Li et al. |
| 6,590,751 | B1 | 7/2003 | Horng et al. |
| 7,053,730 | B2 | 5/2006 | Park et al. |
| 7,560,920 | B1 | 7/2009 | Ouyang et al. |
| 7,696,748 | B2 | 4/2010 | Schlicker et al. |
| 9,099,984 | B2 | 8/2015 | Reinhardt et al. |
| 10,601,400 | B1 | 3/2020 | McConney et al. |
| 2007/0167723 | A1 | 7/2007 | Park et al. |
| 2007/0252593 | A1 | 11/2007 | Takeuchi et al. |
| 2010/0164487 | A1 | 7/2010 | Eyckmans et al. |
| 2010/0253326 | A1 | 10/2010 | Koyilothu et al. |
| 2012/0218060 | A1 | 8/2012 | Burak et al. |
| 2012/0256522 | A1 | 10/2012 | Ito et al. |
| 2012/0280682 | A1 | 11/2012 | Cheng et al. |
| 2013/0165766 | A1* | 6/2013 | Nishikawa ............. A61B 5/245 600/409 |
| 2013/0271145 | A1 | 10/2013 | Hwang et al. |
| 2013/0324832 | A1* | 12/2013 | Wu ........................ A61B 5/242 600/409 |
| 2014/0139213 | A1 | 5/2014 | Cadugan et al. |
| 2015/0318838 | A1 | 11/2015 | Bhattacharjee et al. |
| 2016/0143541 | A1* | 5/2016 | He ........................ A61B 5/374 600/407 |
| 2017/0086681 | A1* | 3/2017 | Passmore ............. A61B 5/0004 |
| 2017/0363584 | A1 | 12/2017 | Tong et al. |
| 2018/0081001 | A1* | 3/2018 | Iwasaki .................. A61B 5/243 |
| 2018/0292468 | A1 | 10/2018 | Guo |
| 2019/0317161 | A1 | 10/2019 | Quandt et al. |
| 2019/0325904 | A1 | 10/2019 | Ramakrishnan |
| 2019/0385586 | A1 | 12/2019 | Salahuddin et al. |
| 2020/0072916 | A1* | 3/2020 | Alford ............... G01R 33/0017 |
| 2020/0334559 | A1* | 10/2020 | Anderson ............. G06N 20/00 |
| 2020/0348378 | A1* | 11/2020 | Alford .................... H05K 1/18 |
| 2021/0041512 | A1* | 2/2021 | Pratt ................... A61B 5/0077 |
| 2021/0181132 | A1 | 6/2021 | Labanowski et al. |

OTHER PUBLICATIONS

L. Dreher et al: "Surface acoustic wave driven ferromagnetic resonance in nickel thin films: Theory and experiment", Physical Review. B, vol. 86, No. 13, Oct. 17, 2012 (Oct. 17, 2012), XP055635289, US ISSN: 1098-0121, DOI: 10.1103/PhysRevB.86. 134415 *Sections I. to III.; figure 1*.

U.S. Appl. No. 17/120,907, filed Dec. 14, 2020, Dominic Labanowski.

Shibayama et al, "Optimum Cut for Rotated Y-Cut LiNbO3 Crystal Used as the Substrate of Acoustic-Surface-Wave Filters", Proc. of the IEEE, vol. 64, No. 5, p. 595-598, May 1976.

Labanowski and Salahuddin, "Effects of Magnetoelastic film thickness on power absorption in acoustically driven ferromagnetic resonance," App Phys. Lett. 111, 102904 (2017); doi: 10.1063/1. 4994933.

Labanowski et al., "Power absorption in acoustically driven ferromagnetic resonance", Appl. Phys. Lett. 108, 022905, (2016).

Labanowski, "Power Absorption in Acoustically Driven Ferromagnetic Resonance", Supplemental Material, 4 pages, (2016).

* cited by examiner

Exterior View          Interior View

| S | Sensor | | Coupler |
|---|---|---|---|
| $\ell$ | Attenuator | | Hybrid Coupler |
| L | Inductor | M | Matching Network |
| γ | Phase shifter | | Field Coil |
| F | Bandpass Filter | (≥) | Comparator |
| (X) | Mixer | Logic | Logic Circuit |
| (A) | Amplifier | | Analog to digital coverter |

FIGURE 13

Enabling a field-measuring device S110

Monitoring device sensors in desired measuring regions S120

Localizing field activity S130

FIGURE 29

SYSTEM AND METHOD FOR A WEARABLE BIOLOGICAL FIELD SENSING DEVICE USING FERROMAGNETIC RESONANCE

CROSS-REFERENCE TO RELATED APPLICATIONS

This Application claims the benefit of U.S. Provisional Application No. 62/966,682, filed on 28 Jan. 2020, and U.S. Provisional Application No. 63/093,700, filed on 19 Oct. 2020 both of which are incorporated in their entireties by this reference.

TECHNICAL FIELD

This invention relates generally to the field of monitoring biological activity, and more specifically to a new and useful system and method for monitoring electromagnetic biological activity using ferromagnetic resonance.

BACKGROUND

Ferromagnetic resonance (FMR) may be used to measures magnetic properties of materials by detecting the precessional motion of the magnetization in a ferromagnetic sample. Different types of FMR include externally-driven FMR and current-driven FMR. FMR can be excited using a variety of techniques, like cavity excitation, stripline excitation, spin transfer torque, and spin orbit torque, among others. These implementations are typically not compatible with device applications. They require large cavities, high power drive, and use large sample volumes in order to be effective. As such, the use of FMR is largely restricted to large laboratory setups and to research projects.

There are several types of highly sensitive magnetic sensors but they all have various limitations. For example, SERF and SQUID magnetic sensing approaches can have high sensitivity but at the cost of being large, complex and difficult for system integration. These sensors require room-size integrations that require heavy shielding to isolate the sensors from ambient and other external fields and strictly maintained temperature conditions for functionality. Alternatively, Hall effect sensors and magnetoresistive sensors may be smaller solutions at the cost of sensitivity and are largely not sufficient for many purposes such as in brain activity monitoring devices.

Magnetic sensors have been used for decades to monitor biological activity. In particular, brain activity. Due to performance requirements, these magnetic sensors are typically SERF and SQUID type sensors. Current SERF and SQUID devices require costly room-sized infrastructure due to their sensitivity to environmental perturbations. These systems are also fairly rigid and can't be adjusted for different sized users. These limitations mean many sites fail to be able to serve a wide diversity of users since its often cost prohibitive to have multiple systems to accommodate different user sizes. Furthermore, such brain activity monitoring devices are limited to stationary measurements.

Thus, there is a need in the field of biological electromagnetic (EM) field monitoring to create a new and useful system and method for monitoring biological EM fields that is more portable, both smaller in size and less limited by environmental conditions, and easier to modify for specific users. This invention provides such a new and useful system and method.

BRIEF DESCRIPTION OF THE FIGURES

FIG. 1*l* is a simplified schematic representation of an ADFMR sensor;

FIG. 13 is a glossary of circuit components;

FIG. 29 is a flowchart of a method of a preferred embodiment;

DESCRIPTION OF THE EMBODIMENTS

The following description of the embodiments of the invention is not intended to limit the invention to these embodiments but rather to enable a person skilled in the art to make and use this invention.

1. Overview

Figure 1:
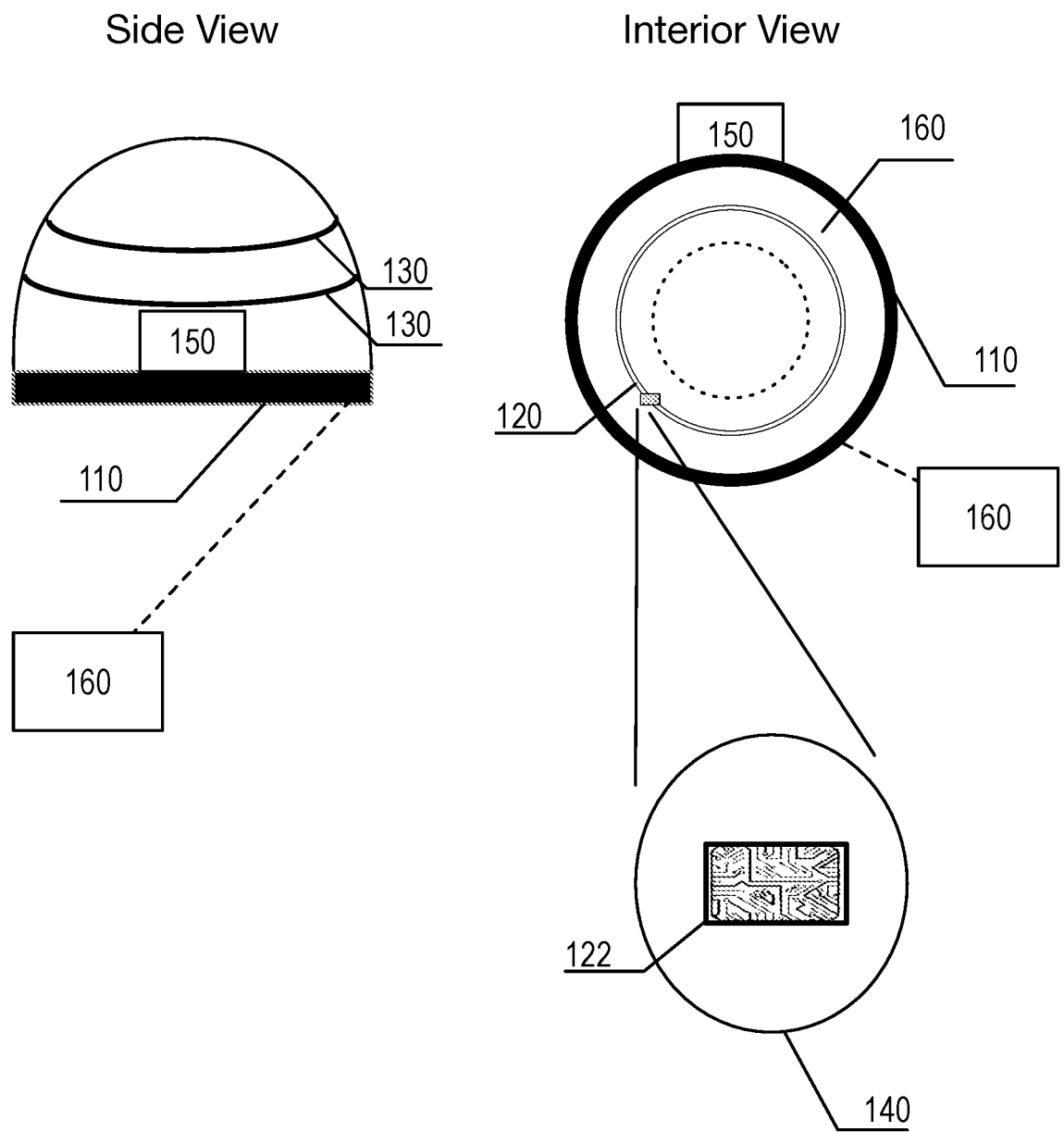
FIG. 1 is one schematic representation of a system a helmet device.

As shown in FIG. 1, a system and method for a wearable device to measure biological EM fields integrates a unique acoustically driven ferro-magnetic resonance (ADFMR) sensor into a wearable form factor. The system and method functions to provide a more flexible and/or portable sensor device. The form factor is preferably designed to fit the contour of a surface region of the body, thereby holding the plurality of sensors, in place, on a surface region of the user. Examples of types of form factors include: helmets, bands (e.g. head, arm, waist), patches, and/or other wearable form factors. The system preferably integrates a plurality of sensors which includes at least one of the ADFMR sensors described herein. The system and method leverage the sensitivity of the ADFMR chip sensors to measure user EM biometric information while positioned proximally to the surface skin of the user. The ADFMR sensor can operate at more normal temperature ranges (e.g., temperatures possibly encountered in daily use by a user such as 0-120° F.) while still maintaining magnetic field sensing capabilities to enable precise monitoring of biological EM fields (e.g., brain activity). The system and method additionally leverage the size of the ADFMR sensors to employ a potentially highly dense array of sensors providing high resolution real-time imaging of biological EM fields, particularly brain, heart, and muscle activity, while enabling ease of use and portability of the device.

The system and method may be implemented as a stand-alone biological field measuring device, and/or with other types of sensors, enabling a more thorough biometric "profile" of the user. The system and method may additionally be implemented as a standalone, or integrated with, brain computing interface (BCI), wherein the system and method provide a method for user sensor input. Examples of additional types of sensors that may be included as part of the system and method include: accelerometers, inertial measurement units (IMUs), digital thermometers, and cameras. Additionally, multiple form factors may be implemented together to enable simultaneous measurements of different regions (e.g. heart and brain). In one variation, additional biosensors such as an electroencephalography (EEG) sensor, a heart rate sensor, blood pressure sensor, a respiratory sensor, a blood glucose sensor, respiratory sensor, a functional near-infrared spectroscopy (fNIRS) sensing system, impedance tomography, other magnetic sensors, and/or other suitable types of biosensors may be used in combination.

The system and method are preferably used for a brain activity device, which may be used for brain monitoring and/or potentially enabling forms of a brain-computer interface (e.g. virtual reality or augmented reality integration). Additionally, applications may use the system and method for biological sensing, such as muscle activity, and monitoring heart activity. Additionally, the system and method including multiple sensor types may be used for high level biometric monitoring and computer interfacing. As both a biometric monitoring device and as computer interface, the system and method may be implemented with or as part of mobile and smart devices. The system and method enable interaction with smart phones, watches, glasses, or any other smart devices. The power efficiency of the system and method can further enable mobile applications of the biological monitoring capabilities of the system and method.

The system and method enable a significant number of technological enhancements that allow functionality and benefits beyond what is available in current devices. One potential benefit of the system and method is that ADFMR sensors may function at room temperature. Most field sensors that have at least equivalent levels of sensitivity (e.g. SQUID) must function at significantly lower temperatures with limited room for temperature variations, require magnetic shielding to operate, or are substantially larger in size. For example, the ADFMR sensors of the system and method do not need temperature control systems maintaining temperatures near absolute zero as with traditional SQUID brain activity monitoring devices.

Additionally, due to temperature and other factors, current brain activity sensors cannot be placed adjacent to the scalp of a user (e.g. at least 4-5 cm displacement is required for SQUIDs). The wearable ADFMR device does not have this disadvantage and can have sensor nodes directly on the scalp of the user.

Having sensors adjacent to the scalp of a user may confer another potential advantage. More specifically, other sensor devices typically require a noise density below ~10 fT/sqrt (Hz) to measure signals originating from the brain, while the system and method may operate with noise density of ~10 pT/sqrt(Hz). This potential benefit may be enabled in part by increased sensor density and sensor proximity to the scalp. This in turn may lead to the potential benefit of a system and method that requires significantly less power. The system and method may additionally more efficiently monitor brain activity in a power efficient manner by localizing the operation of sensors. For example, the system and method may operate in a mode for activity localization while sensing in a low power mode. Once a location of interest is identified, the sensors in appropriate position for sensing can be operated in a mode for high quality data collection, while other sensors are temporarily disabled or operated in a low power mode.

Additionally, there are many potential benefits in that the ADFMR chip sensors may be built to include specialized components or enhanced functionalities not easily implementable in other sensor devices. Examples include: low power usage, noise cancellation, and field strength optimization.

One potential benefit of a specialized ADFMR chip sensor is that it may include noise cancellation. An ADFMR chip sensor that includes noise cancellation may require significantly less shielding and noise cancellation from external fields (e.g. earth's magnetic field) for accurate readings.

Additionally, ADFMR chip sensors employed in a dense array may also add to the potential benefit of significantly reducing the need for passive or active noise cancellation. The dense array of sensors may add a sufficient number of sensor readouts such that the noise may be averaged out over all the sensor readings or otherwise eliminated through digital signal processing.

Another potential benefit of a specialized ADFMR chip sensor is less power usage. At the expense of some sensitivity, an ADFMR chip sensor may, in some variations, be designed to use significantly less power at least in certain periods of time. Lower power usage ADFMR chip sensors may lead to a benefit for a device that can be significantly more mobile and less power reliant. For example, when implemented in a device for epileptic seizure monitoring, the device may primarily be operated in a low power mode to monitor for a particular pattern, and when a spike in activity is detected the device can transition to a higher resolution monitoring mode for capturing activity during the seizure event. For example, the device may be used to measure activity during a spike in activity indicating some event such as during an ictal period indicative of a seizure.

Current systems with equivalent sensitivity for measuring magnetic fields, typically have a small range over which they can measure magnetic fields and magnetic fluxes. Another potential benefit of the system is that ADFMR chip sensors may accurately measure fields and gradients over magnitude much larger field range.

The portability of the device may also convey several benefits. As one potential benefit, the small size of the device may enable the system and method to be implemented more precisely for different size individuals (e.g., children vs. adults). Additionally, the small size enables easier implementation for very localized measurements over a surface. For example, implementing the system and method as a headband for measuring a "band" of brain activity instead of a helmet measuring all brain activity.

As another potential benefit of the portability, the system and method may enable a user to "wear" the device such that the system and method may include continuous real-time monitoring of biometric activity during normal "living". As such the system and method can be used in a way that can support movement by the user.

As another potential benefit of the portability, the device enables the system and method to be used in conjunction with smart devices or other interactive devices, such as smart watches, smart phones, etc.

As another potential benefit of the portability, the system and method enable a "simpler" integration as a BCI, such that a highly variable number of sensors may be incorporated over the brain for potentially diverse implementations. In this manner, the system and method enable integration with current commercial hardware (e.g. gaming headsets, headphones, vehicles, etc.)

As a wafer-scale manufacturable sensor device, the system and method provide the potential benefit of a low-cost, high-volume production device. This is in direct contrast to many similar sensitive magnetometers on the market today. For example, current SQUID sensors cannot currently be manufactured in sufficient volume to distribute to millions of people. In some variations of the system and method, multiple FMR sensors (e.g., more specifically ADFMR sensors) may be integrated as a system-in-package (SiP) device where multiple systems, such as the microelectromechanical systems (MEMS) of the ADFMR sensor element and/or read-out/signal processing integrated circuits, may be packaged and enclosed in one or more chip carrier packages (e.g., a surface mount circuit package). In some such implementations, a system on a chip (SoC) implementation may enable such a FMR sensor device on a single semiconductor die/wafer. Such integrations may enable unique technical capabilities while also being more usable and manufacturable.

2. Wearable Sensor Device System

As shown in FIG. 1, a system for a wearable field sensing device for biological electromagnetic (EM) field measurement includes: a wearable structure 110; a biological sensor array 120, on or within the wearable structure, such that each biological sensor is situated adjacent to the body of the user, and wherein each biological sensor includes at least one ferromagnetic resonance (FMR) sensor; a power system 150, providing the power for the system; and a control circuitry 160, electrically coupled to the system. In some preferred variations, the FMR sensor comprises an acoustically driven ferromagnetic resonance (ADFMR) sensor 122.

The system can be integrated into various types of devices such as augmented reality (AR) glasses, virtual reality (VR) headsets, smart headphones, hearables, smartwatches, smart rings, smart wearables, health fitness trackers, chest strap heart monitors, brain scanner systems (e.g., for medical device integrations), eye tracking devices, and/or other suitable devices. Additionally, the system may be integrated as part of a brain computer interface (BCI) wherein the system may leverage cranial sensor data as part of an interactive operation.

The system functions as a wearable sensor device that measures electromagnetic (EM) fields within a user and can further identify the source of the EM field with sub-centimeter precision. In this manner, the system may function to identify cellular activity, such as brain activity, nervous system activity, muscle movement, blood flow and/or any other electrical or electrochemical biological activity. The system may be implemented for a human user and/or patient, but may be also implemented for any other animal types (e.g. cats, horses, lizards). In some variations, the system may include multiple wearable sensor devices. Multiple wearable sensor devices may function to simultaneously measure EM fields of a user along multiple regions of the user.

The device activity may be implementation specific. As a device worn on the head (e.g. a cap or headband wearable structure no), the system may be implemented as brain computer interface (BCI) device that enables direct, or virtual, interactions. Additionally, or alternatively, the cap may serve as a medical device to monitor the brain activity of a patient.

Dependent on the implementation the system may have additional or alternative components. Examples of additional components may include additional sensor components (e.g. external field sensors to measure external magnetic field for noise cancelling, a gyroscope to measure a wearer's positioning, a thermometer to measure the temperature of the user) and sensor shielding 140, to improve sensor measurements. The system may additionally, or alternatively, include any other desired component. Examples of sensors that may be included as part of the system include, but are not limited to: IMUs, EEG sensors, gyroscopes, accelerometers, non-ADFMR magnetometers, and thermometers.

In some variations, the system includes an ambient sensor array 130, situated on the wearable structure 110. The ambient sensor array 130 may comprise sensors situated on, or near, the wearable structure configured to measure ambient EM fields in proximity of the wearable structure. The ambient sensor array may comprise field sensors that measure external EM fields. Dependent on implementation, these sensors may, or may not, comprise FMR sensors.

The wearable structure no may function as a housing for other system components, particularly the biological sensor array 120; wherein the wearable structure holds the biological sensor array in proximity to a desired measuring area on the user. The wearable structure no may be worn/wrapped/adhered, or positioned in another manner such that one surface of the wearable structure factor no is in direct contact with a wearer. The wearable form factor no may have any desired general form, but will, generally speaking, have an "interior" defined shape to match the contours of the wearer (e.g. the interior of a cap wearable structure, or the interior surface of a patch wearable structure). In many variations, the wearable structure may define the type and activity of the system. For example, a headwear wearable structure no may be used for measuring brain activity (e.g. as part of a BCI device); a heart patch wearable structure may be used for heart, or blood flow, monitoring; a leg band may be used to measure the type and strength of leg muscle contractions.

The system may have different implementations, or combinations of implementations such that the wearable structure 110 fits to the contour of the body of the user in the desired region(s) of activity measurement. In one implementation, the wearable structure 110 is specifically built to fit the contour of a user. In a second implementation, the wearable structure 110 may be composed of stretchable material (e.g. elastics such as rubber) to stretch over the contour of the user. In a third implementation, the wearable structure no may be malleable, or semi-malleable (e.g. soft metals such as aluminum), such that the wearable structure no may be "deformed" to fit the contour of the user. In a fourth implementation, the wearable structure no may comprise modular subcomponents, wherein the wearable structure no is "built" on the user to fit the contour of the user. In variations where the size of the wearable structure no can be adjusted, the wearable structure may come in general sizes (e.g. adult, child, small, large, etc.) that may, or may not, then be further adjusted for a particular user. In variations wherein the wearable structure 110 is somehow deformable (e.g., stretchable or malleable) the wearable structure may comprise deformable regions that may change in size and rigid regions that do not change in size and shape. Rigid regions may enable fixed positionality for sensors placement.

The system of claim 2, wherein the wearable structure comprises an adherable patch, wherein the adherable patch is shaped to, at least, partially cover a user body region for EM field measurement.

The wearable structure 110 shape may be implementation specific. In one variation the wearable structure 110 comprises a portable cap. In another variation, the wearable structure 110 comprises a patch. Example shapes of the wearable structure 110 include: helmet, headband, wristband, leg-band, girdle, and form fitting patch. As described before, these shapes may be built to fit the user contour, stretchable, malleable, and/or modular as desired by implementation. In some variations, the wearable structure may be personalized. For example, the wearable structure 110 may be 3D printed to precisely match a specific person's head shape.

In one preferred variation, as shown in FIG. 1, the wearable structure 110 is shaped as a helmet or portable cap. The cap structure 110 may enable measuring brain activity over the surface of the brain, throughout the entire brain, or part of the brain. The portable cap may comprise a cap shaped to, at least, partially cover a head region of a user for EM field measurement. The cap structure may function as a BCI for activities and/or as a medical device. In one implementation, the cap structure is part of a flight simulator interface. As a cap, the wearable structure 110 preferably fits to the contours of the head. The cap may be both adult or child sized. In some variations, the portable cap comprises a deformable cap such that the deformable cap may sufficiently change in size and shape to fit the head region of the user, wherein the deformable cap comprises deformable regions that may change in size and shape and rigid regions that do not change in size and shape. In some variations, the wearable structure 110 is designed so that whole brain activity can be sensed with a distributed biological sensor array 120. Alternatively, the structure 110 may be designed so that activity can be measured for one or more select regions of the brain such as the motor cortex, visual cortex, auditory cortex, prefrontal cortex (speech), parietal lobe, and/or other regions.

Alternative wearable structure 110 form factors may be used to collect measurements over other regions such select muscle regions or the heart. In one variation, the wearable structure 110 is shaped as a band, e.g. sweatband, headband, arm-band, leg band, waistband, etc. The band wearable structure 110 may enable field activity measurement over a localized region in proximity of the band. As desired for implementation, the band wearable structure 110 may comprise a closed loop, or a crescent shaped body wearable structure 110. In one preferred implementation, as a crescent shaped body headband, the wearable structure 110 may be worn on the head to measure brain activity across a specific band, or region, of the head.

Figure 2:
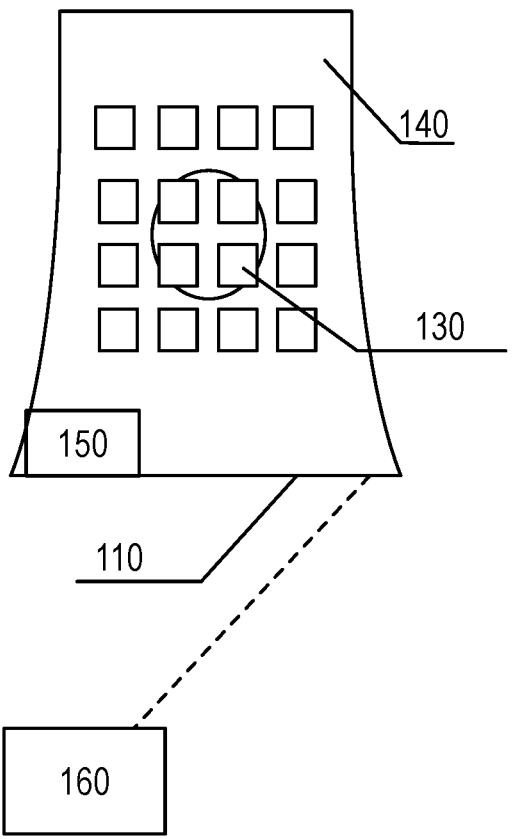
FIG. 2 is an alternate schematic representation of a system of an adherable patch.
Figure 2:
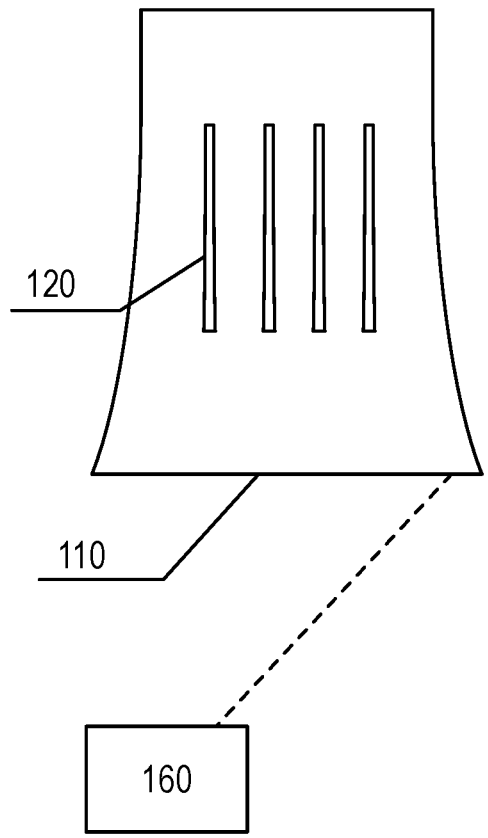

In a third variation, as shown in FIG. 2, the wearable structure 110 is a patch. The patch wearable structure 110 may function to enable field measurement in a localized "patch" region. The patch wearable structure 110 may have any generalized shape and/or size. The patch may be attached to the user at the desired region through the use of adhesive, elastic band, or through some other method. One implementation of the patch wearable structure 110 includes a patch worn on the chest area to measure/monitor heart activity. Another implementation of the patch wearable structure 110 includes a patch on a major muscle group (e.g. calf muscle), enabling the measurement/monitoring of muscle activity in that region.

The biological sensor array 120 comprises an array of EM sensors situated on the "interior" wearable structure, and capable of measuring EM fields. The biological sensor array 120 may function to measure EM fields in, or on, the body of the user. That is, each EM sensor from the biological sensor array 120 may measure EM fields in proximity of the positioning of the sensor on the wearable structure 110. In some variations, the EM sensor comprise FMR sensors. More preferably, the FMR sensors comprise ADFMR sensors, wherein the biological sensor array 120 comprises an array of ADFMR sensors 122. In preferred variations, the EM sensors comprise chip-scale sensor implementations, which may enable a high density of sensors to be integrated as part of the biological sensor array 110.

The number of sensors comprising the biological sensor array 122 may vary in orders of magnitude dependent on implementation. In one virtual reality (VR) interaction implementation, the number of sensors may be on the order of 10-20 sensors. In another, patient monitoring, implementation the number of sensors may be on the order of 10,000. In a heart monitoring variation, the number of sensors may be 2-3 sensors. Preferably, the biological sensor array 120 includes a plurality of sensors. In an alternate preferred variation, the biological sensor array S120 may comprise only a single sensor. This variation may be implemented in use cases where simple localized monitoring is sufficient (e.g., as a heart-rate monitor).

Sensors of the biological sensor array 120 may be implemented on, or in combination with, an integrated circuit (IC) as part of an integrated circuit package (or collection of IC packages). In some variations, such an IC packaged sensor device may include a wafer-scale manufacturable sensor device. The size and form-factor of such sensor devices may enable a larger number and potentially higher density of sensors. In particular, the biological sensor array 120 may include one or more ADFMR sensor elements. The ADFMR sensor elements may be a packaged sensor unit such as a through-hole IC chip and/or a surface mount IC chip, which can be integrated into a rigid or flexible printed circuit board (PCB), a wired circuit, and/or other types of circuit systems. The ADFMR sensor may also be co-packaged with an integrated circuit chip. Alternative packages or form-factors may also be used.

ADFMR sensors in one preferred embodiment may be fabricated using high-volume, high-throughput manufacturing techniques. An example of such techniques are standard semiconductor or MEMS fabrication techniques. Some examples of such techniques are wafer-scale processing techniques such as photolithography, etching, and deposition (via electron beam evaporation, sputtering, or other similar processes), which allow for the parallel fabrication of many devices. These techniques allow for high-yield production of extremely large volumes (allowing for volumes as high as millions of units per month or more) at extremely low cost (potentially a dollar per unit or less). Wafer-scale production also allows the usage of wafer-scale testing techniques (for example automated probe stations) that can accelerate QA, testing, calibration, and development processes.

A variety of sensor form factors leveraging the high volume manufacturability possibilities of the ADFMR sensors may be used. These various form factors can decrease cost of production as well as enable higher numbers and/or density of sensors to be implemented within the system.

In one variation, an ADFMR sensor can include one or more ADFMR sensor element(s) integrated with and used in combination with an integrated circuit implementation of associated ADFMR signal processing circuitry. As described below, the ADFMR signal processing circuitry may include excitation circuitry, detection circuitry, circuitry for noise reduction/output signal conditioning, and/or other portions of circuitry used in collecting ADFMR sensor data output. Variations may have the ADFMR sensor element(s) and the ADFMR signal processing circuitry co-packaged or packaged/implemented as distinct chip/circuit components.

The ADFMR sensor element may be implemented separately from ADFMR signal processing circuitry. For example, the ADFMR sensor element may be an ADFMR sensor chip that can be used in combination with other ADFMR signal processing circuitry components. Regardless of how the ADFMR sensor element is integrated, some variations of the ADFMR sensor element may still leverage wafer-scale fabrication techniques.

In one possible variation, the ADFMR signal processing circuitry could be implemented, in part or whole, as an application-specific integrated circuit (ASIC) or an application-specific standard product (ASSP) integrated circuit or any suitable type of integrated circuit. The ASIC form factor (and/or other comparable form factors) may be built using CMOS processing techniques and may additionally enable the size of the ADFMR sensor to have the circuitry components miniaturized to millimeter scale dimensions. One or more ADFMR sensor elements and the ADFMR signal processing ASIC may be co-packaged into an ADFMR sensor unit (i.e., an ADFMR sensor chip). In one such variation, the ADFMR sensor can be a system-in-package (SiP) that includes one or more ADFMR sensor elements and an ASIC. In another variation, an ADFMR sensor unit can be a system on a chip (SoC) including an ASIC with one or more integrated ADFMR sensor elements.

In some variations, the ADFMR sensor element may be implemented as part of the same ASIC or as a separate ASIC.

Additionally or alternatively, in some variations, the ADFMR signal processing circuitry could be implemented in part or whole as a PCB implementation of the ADFMR signal processing circuitry.

Additionally, preferred variations of the ADFMR sensors used as the EM sensor elements may be room temperature operable without temperature control and as such may include cryogen-free operation as compared to other types of field sensors (e.g., SQUID sensors). Additionally, preferred variations of the ADFMR sensor can operate without vapor cells or heated vapor cells as compared to other types of field sensors (e.g., SERF or OPM sensors). These properties can enable unique technical capabilities while also being more usable and manufacturable.

In one variation, the biological sensor 120 array comprises 1-10 sensors (e.g. heart-rate monitor). In another variation, the biological sensor 120 array comprises 10-100 ADFMR sensors (e.g. as part of a BCI). In another variation, the biological sensor array 120 comprises 100-1,000 ADFMR sensors (e.g. a portable brain scanning device). In another variation, the biological sensor array 120 comprises 1,000-10,000 ADFMR sensors (e.g. clinical brain scanning device). In another variation, the biological sensor array comprises 10,000-100,000 ADFMR sensors. Such large scale sensing devices may employ machine learning and/or other analysis models for interpreting/classifying signals.

Additionally, machine learning and/or other data models may also be used to dynamically adjust control of sensors such as by dynamically activating different subsets of sensors depending on previously sensed data, system state, and/or input from an external system.

The positioning and distribution of the biological sensor array 120 may be implementation dependent. In one variation, the biological sensor array 120 includes sensors that are evenly distributed along the wearable structure 110, or specific regions of the wearable structure. In a second variation, the sensor array may include dense distributions along regions of the wearable structure 110 that correspond to desired regions of measurement on a user (e.g. a high density of EM sensors on the back of the head for visual cortex measurement). Different concentrations and arrangements of sensors can be positioned within the cap wearable structure no to cover activity of distinct regions of the brain. In a third variation, the wearable structure may include varying degrees of distribution (e.g. wherein the density distribution is dependent on expected type of activity in that region). In variations wherein the wearable structure 110 is somehow deformable (e.g., stretchable or malleable) the wearable structure may comprise deformable regions that may change in size and rigid regions that do not change in size and shape. In these variations, the biological sensor may be situated on the rigid regions. In this manner, sensors comprising the biological sensor array 120 may maintain a known displacement from each other. Alternatively, the biological sensor array 120 may be positioned on deformable regions. In these variations, the positioning of the biological sensor array 120 may be determined dynamically (e.g. through the use of positioning sensors).

The biological sensor array 120 may include a position pattern that is distributed across the whole monitored area or alternatively distributed across localized regions. A position pattern could be a regular rectangular grid, a circular arranged array, or any suitable pattern. Custom position patterns may also be used where positions are adapted for monitoring key regions. The regions of monitoring that are covered by the biological sensor array 120 may also be any suitable form such as a square, rectangle, circle, oval, or any suitable shape. This may be used to cover different regions and to increase the sensed signal from different regions of interest.

In some cases, the sensors may be distributed so as to enhance capabilities for using synthetic gradiometry to improve the sensor signals. As one optional variation, the biological sensor array 120 may be clustered in small dense patches that are spaced apart. The displacement between the clusters can enable sensors to be subtracted so as to remove environmental noise but keep more of the signal. For example, as opposed to one large dense collection of sensors over an area, multiple clusters could be used where sensor density is high inside the cluster and the clusters are spaced apart. As another example, a large dense cluster of sensors may be positioned in a region of interest, and then a select number of sensors may be spaced apart from the cluster (e.g., 4 sensors encircling the cluster spaced 2 cm away). This approach of displaced clusters can enable averaging within the small dense sensor clusters but then the distance between the clusters can enable effective gradiometry by comparing further sensor clusters.

In some variations, the biological sensor array 120 may include discrete sensor array components including connectors such that they sensors of the biological sensors array are positionally configurable within a wearable structure no form factor. There may be multiple sensor array components that are used in combination as part of the biological sensor array 120. In some variations, there can be a combination of statically positioned sensors and repositionable sensor components.

A positionally configurable sensor array component may function to provide flexibility in the placement of at least some sensors of the biological sensor array 120. The position adjustments may be made manually (e.g., removing a sensor component from one position and attaching to another optional position) or through an automated actuation element. As another application of removable sensor array components, a sensor array component may enable easier maintenance or configuration. For example, a sensor array component may be replaced if there is a bad sensor. In another example, a sensor array component with one configuration (e.g., number of sensors, configuration sensors, arrangement, etc.) can be exchanged for a sensor array component with a second sensor configuration (e.g., a higher density of sensors). In a similar fashion, use of sensor array components can enable the capabilities of the system to be expanded. For example, a system originally configured with a sensing in one localized region of the brain may be expanded to monitor multiple regions of the brain through the addition of sensor array components.

In some variations, the sensors of the biological sensor array 120 may serve different functionalities. For example, a sensor or cluster of sensors may be used as one, or multiple, reference sensors. Reference sensors may primarily be used for improving sensor signals, gradiometry measurements, noise cancellation, or other techniques. For example, reference sensors may be placed on any suitable position of the body. In noise cancellation implementations, the reference sensors may be positioned on the wearable structure outside of the region that is to be monitored. The reference sensors may then measure biological background noise that would then be subtracted from the desired measurements. In some situations, this location may be completely removed from the portion of the body of interest. In some variations, it may be electrically connected. For example, a wired connector, used to relay power and/or communication may connect a reference sensor to a main portion of the system. In some variations, a reference sensor may be wirelessly integrated into the system by collecting reference data and communicating the collected data to computer processor system (on the worn device or off) used in collectively analyzing data and/or managing operation of the system.

Each sensor comprising the biological sensor array may be identical or distinct. In variations, each sensor may be similar or identical FMR sensor. In preferred variations, each FMR sensor an ADFMR sensor 122 as discussed below. Each sensor, preferably contains at least one field sensor, although it may contain multiple field sensors. Additionally, the configuration of the sensors in the biological sensor array 122 may be made substantially uniform or vary with different configurations.

In some variations, one, some, or all, sensors of the biological sensor array 120 comprise ADFMR sensors 122. The ADFMR sensor functions to utilize highly sensitive ferromagnetic resonance to measure magnetic fields. That is, the ADFMR sensor 122 propagates acoustic waves on the surface of a piezoelectric substrate, wherein the interaction between the acoustic waves and a magnetostrictive element is strongly dependent on magnetic fields. In presence of an EM field, propagating acoustic waves are altered in proportion to the strength of the field, thus enabling measurement of the field. Additionally, the ADFMR sensor 122 may be produced using semiconductor/MEMs manufacturing techniques, enabling the incorporation of a high density of field sensors as desired (e.g., multiple ADFMR sensors 122 may be included on a single integrated circuit).

Dependent on implementation, and as described below, each implemented ADFMR sensor 122 may be identical or unique. For example, an ADFMR sensor 122 for gradiometry measurements may include different circuitry than a low power ADFMR sensor, or an ADFMR sensor including noise cancellation coils. In alternate implementations, each sensor may include multiple ADFMR sensors of varying numbers as desired. In addition to providing more sensor nodes to measure the EM field, multiple ADFMR sensors may enable multi-dimensional field measurements and field gradient measurements. Multiple ADFMR sensors may alternatively enable other functionalities. In one example, each sensor has three ADFMR sensors. Preferably the three ADFMR sensors are orthogonal to each other, enabling three-dimensional measurement of EM fields. In a second example, the sensor may include at least two ADFMR sensors along the same orientation. Multiple ADFMR sensors along the same orientation may enable measurement of the gradient of the EM field. In a third example, each sensor may have ADFMR sensors in all orientations (same and different), enabling measurement of the EM field, the gradient of the field, and provide noise cancellation circuitry.

In some variations, the system may include an ambient sensor array 130. The ambient sensor array 130 functions as a sensor array configured to measure ambient EM fields in proximity of the wearable structure 110. That is, the ambient sensor array 130 may function as reference sensors to improve biological field measurements. The ambient sensor array 130 may thus be structurally equivalent to the biological sensor array 120, with the distinction that the ambient sensor array is situated and configured to measure "external" EM fields whereas the biological sensor array is situated and configured to measure "internal" (biological) EM fields. Thus, depending on implementation, none, some, or all sensors from the biological sensor array 120 may also comprise/function as part of the ambient sensor array.

In one variation, the ambient sensor array 130 is situated outside of the wearable structure no to measure ambient fields (e.g. situated on the outside of a portable cap).

In another variation, the ambient sensor array 130 is situated on a distinct wearable structure no, such that the biological sensor array 120 and the ambient sensor array are situated on distinct wearable structures. That is, the ambient sensor array may be integrated into a discrete device that is physically separate, though there may be a communicative link between sensor devices. For example, a device for measuring brain activity may be worn on the head, while an ambient sensor may be attached or worn on the wrist, shoulder, chest or another part of the body. In another variations, an ambient sensor may be positioned off the body. For example, an ambient sensor (or sensors) may be positioned somewhere else in the environment such as near a particular device acting as a source of noise.

As mentioned above, the ambient sensor array 130 may comprise similar or identical type sensors as the biological sensor array 120. For example, at least a subset of sensors from the ambient sensor array 130 may comprise FMR sensors. In one implementation, the at least one subset of FMR sensors comprise ADFMR sensors. Additionally, or alternatively, the ambient sensor array 130 may comprise other types of field sensors. For example, in one implementation, at least one subset of sensors from the ambient sensor array 130 comprise magnetometers.

In desired variations, the system may include additional types of sensors and sensor components that measure other, non-EM field metrics. These additional sensors and sensor components may be incorporated as part of the biological sensor array 120, the ambient sensor array 130, or as distinct components. As part of the sensor arrays, these sensor components may be wafer-scale manufacturable sensor devices such as the IC options described above for the ADFMR biological sensor variations. Additional sensors may further comprise additional components and/or sub-components for additionally desired functionalities (e.g. location detection, motion detection, temperature detection, EM field gradient measurement), and improved functionalities (e.g. noise reduction, SNR amplification, reduced power usage, improved EM field measurement. Accordingly, the system may include various types of biometric, positional, or other types of sensors such as: inertial measurement units (IMUs), digital thermometers, EEG sensors, a heart rate sensor, blood pressure sensor, a blood glucose sensor, a respiratory sensor, a functional near-infrared spectroscopy sensing system, impedance tomography, other magnetic sensors, GPS receivers, IR sensors, cameras, radar, and/or other suitable sensing systems.

These additional sensors may be used in coordination with the data input from the biological sensor array 120. In one variation, biomechanical measurements provided by an inertial measurement unit can be synchronized with the brain activity data to identify and/or isolate portions of the brain activity based on user movement. For example, depending on the application, detected brain activity resulting from physical activity may be removed from analysis or identified and selected for analysis. Additionally, sensors may be used to identify and remove unwanted external signals (e.g. noise). For example, knowledge of device movement and orientation may be utilized to better filter out the magnetic field of the earth. As another example, a camera could be used to watch for blinks or other actions. Detection of a blink (or other corresponding action) could be used to remove activity from associated magnetic/electrical signals. In another variation, the use of supplementary sensing technology can be used to address power routing and/or heating issues.

Additionally, the sensors may include or be used with other computing related components and processing circuitry, such as communication antennas, microprocessors, signal amplifiers, bandpass filters, attenuators, inductors, phase shifters, couplers, mixers, matching networks, analog to digital converters, and comparators.

In some variations the system may include sensor shielding 140. Sensor shielding 140 may function to improve sensor functionality by decreasing noise. Sensor shielding 140 may leverage shielding components to improve functionality, accuracy, and/or precision of the field sensors. Sensor shielding 140 may include shielding components for: each sensor of the biological sensor array 120, for groups of sensors, and/or for the entire system. As another component of shielding, the sensors may be oriented so as to minimize or reduce the effects of external magnetic fields.

In some variations, the sensor shielding 140, or parts of the sensor shielding, are composed of a high permeability metal alloy. The high-permeability metal alloy may function to filter static external fields and fields of specific frequency ranges (e.g. low-frequency magnetic fields). The high permeability metal alloy can have any desired geometry (e.g. as a coil Faraday cage). An example of high permeability metal alloys may include mu-metal.

In some variations, the sensor shielding 140 includes a Faraday cage. The Faraday cage may function to passively cancel dynamic external field noise, e.g. the effects of local transmitters. In one example a conductive mesh is used as a Faraday cage, wherein one, or more, sensors are positioned underneath the conductive mesh. In some variation the sensor shielding 140 includes a mu-metal coating or covering. The mu-metal coating may function to passively cancel static, and/or dynamic magnetic fields (e.g. the magnetic field of the earth). In one example, one, or more, sensors of the biological sensor array 120 are covered, or encased, by a mu-metal covering. This covering may comprise a sheath, a coating ("e.g. painted on), a solid structure (e.g. a box situated on wearable structure 110), and/or any other desired shape that enables shielding of the sensors.

In some preferred variations, the sensor shielding 140 includes a cooling system. The cooling system functions to prevent, counteract, and/or dissipate undesired heat generated by system components, e.g., field sensors. The cooling system may comprise: fans, cooling chemicals, water cooling, heat sinks, and/or any other desired implementation for cooling. In one preferred implementation, the cooling system includes a heat sink. The heat sink is preferably positioned on the external surface of the wearable structure 110, but may alternatively be positioned in a different location that enables dissipation of heat.

In some implementations, the sensor shielding 140 may substantially isolate the sensor. Specially designed electrical feedthroughs optimized to minimize negative impacts on shielding (i.e., optical feedthroughs or electrical feedthroughs that incorporate mu-metal) may be used for control. The control signals for the magnetic sensors can additionally be configured for operation outside the frequency range of the band of interest. For example, a control signal may be mixed up to shift the frequency range bandwidth outside the frequency range of interest for the magnetic sensors. In some variations, optical connections may be used to further enhance the isolation and shielding to external noise for the sensors.

Figure 3:
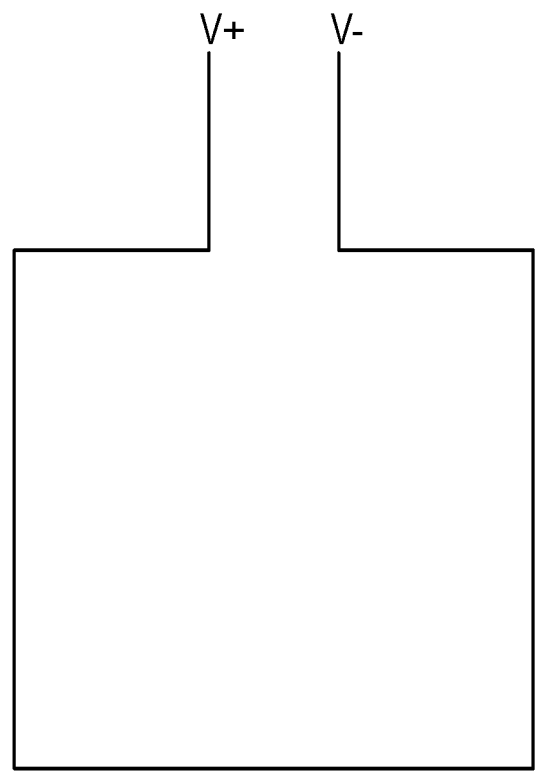
FIGS. 3-5 are variations of schematics for field coils.
Figure 4:
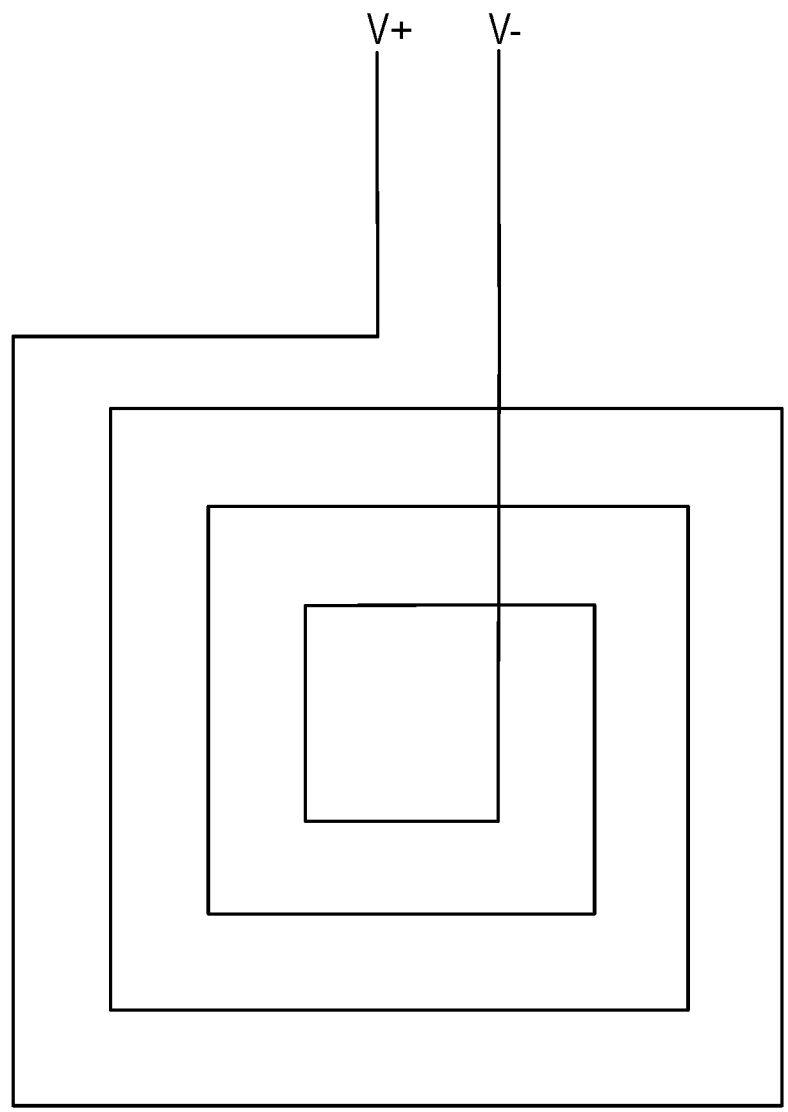
Figure 5:
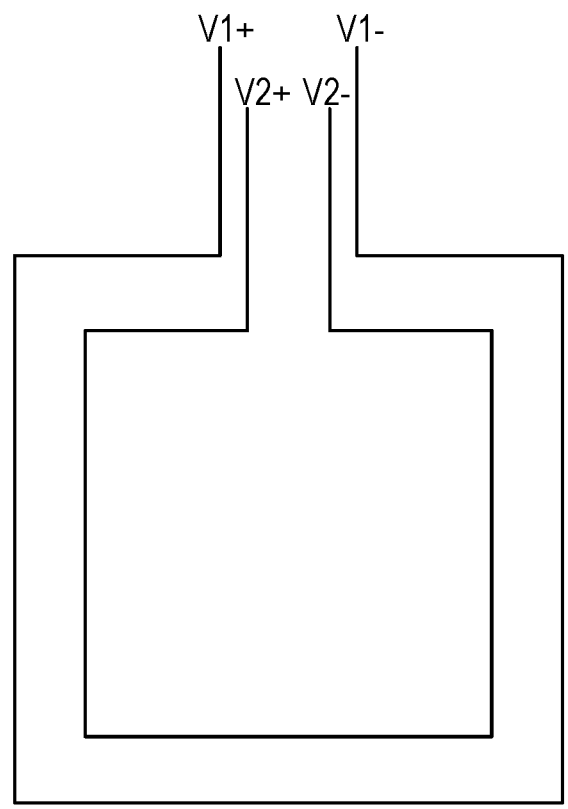

In some variations, the sensor shielding 140 includes field generating coils. Field generating coils may function to shield sensor components by generating a field to counter external fields. The number and shape of the field generating coils may be implementation specific. In one variation, as shown in FIG. 3, the field generating coils comprise single coils, wherein a current through the coil may create an electric field. In a second variation, as shown in FIG. 4, the field generating coils comprise multiple loop coils. In this variation, the coil resistance may be higher, but a greater field per current may be possible. In another variation, as shown in FIG. 5, multiple distinct coils may be overlaid, wherein each coil may be driven separately. In this variation, the field generating coils may be implemented for gradient cancellation and generating of higher order fields. In another variation, the field generating coils may comprise a combination of the prior coils (e.g., multiple coils with multiple loops).

Electric current driven through the coil may be used to create a magnetic field that potentially cancels out external and ambient fields. Thus, the sensor shielding 140 preferably functions with the ambient sensor array 130. For example, in one implementation the sensor shielding 140 field generating coils may work in conjunction with an externally positioned magnetometer. The magnetometer is preferably positioned relatively close to, but external to other major system components (e.g. on the exterior of the wearable structure 110). That is, the magnetometer measures the EM fields external to the wearable structure 110, thus measuring only the external fields (i.e. noise) and no desired signal. Identification of the magnitude of undesired external fields may enable finding and filtering external noise. The magnetometer may be axial, planar, or both. Once the magnitude of the undesired external fields is determined, the field generating coils may generate a "cancelling" field to cancel out the measured fields.

Figure 6:
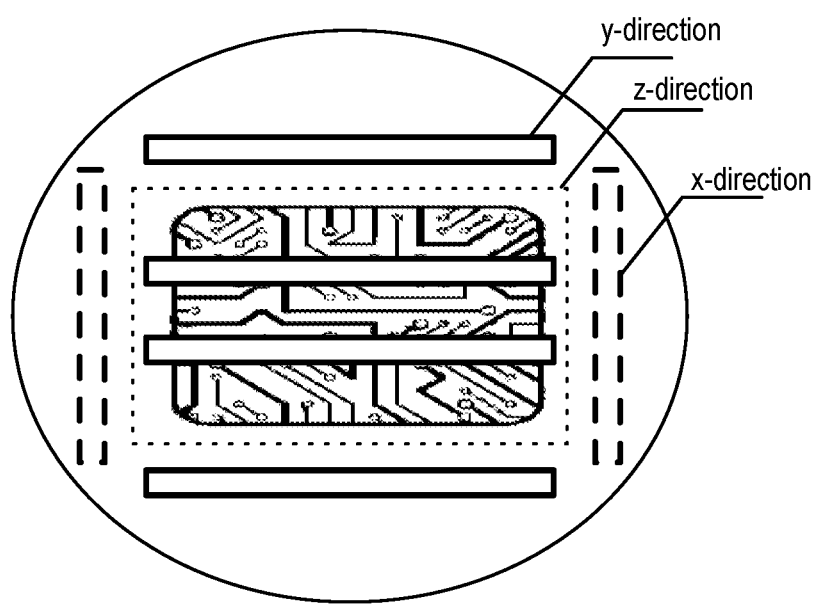
FIG. 6 is a schematic of field coils implemented on a sensor circuit.

Field generating coils may be implemented per biological sensor, as shown in FIGS. 1 and 6 as a group of coils covering/protecting a region of the wearable structure 110 or may be used along the entire wearable structure. Depending on the dimensionality of the desired measuring region, and/or the dimensionality of the wearable structure, the sensor shielding may be implemented as a more expansive set of coils that potentially shield a region, or the entire wearable structure. Concurrently, for more complex (i.e. greater than one dimension) field coils may be positioned such that their coils potentially cancel out all dimensions of external fields.

Figure 7:
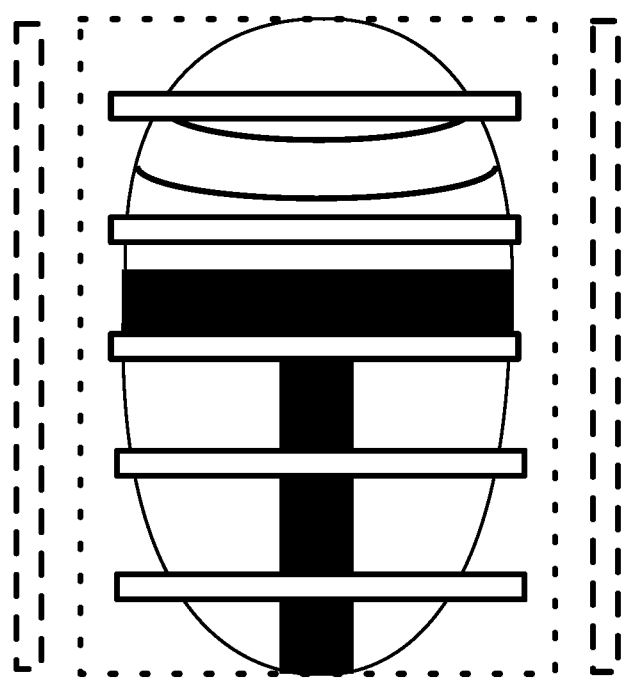
FIGS. 7-9 are variations of schematics of field coils implemented on a helmet device.
Figure 8:
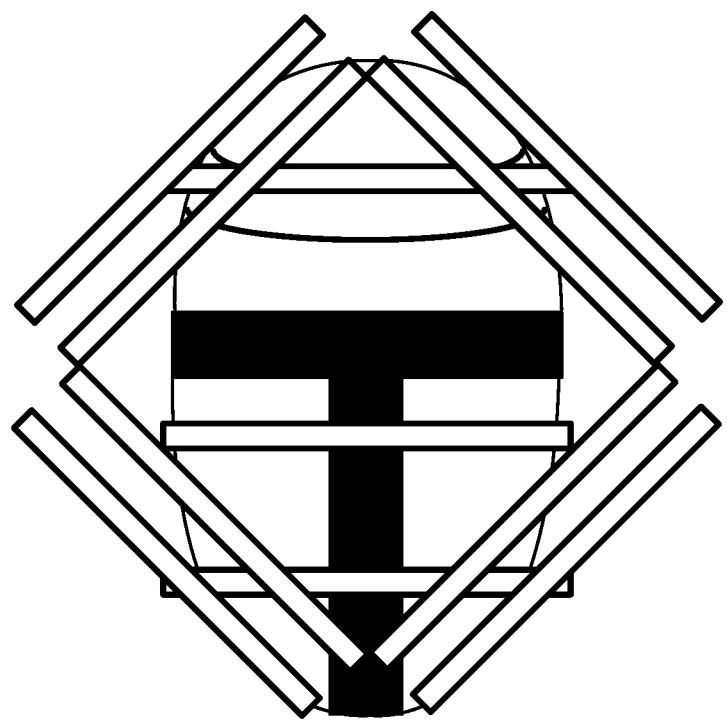
Figure 9:
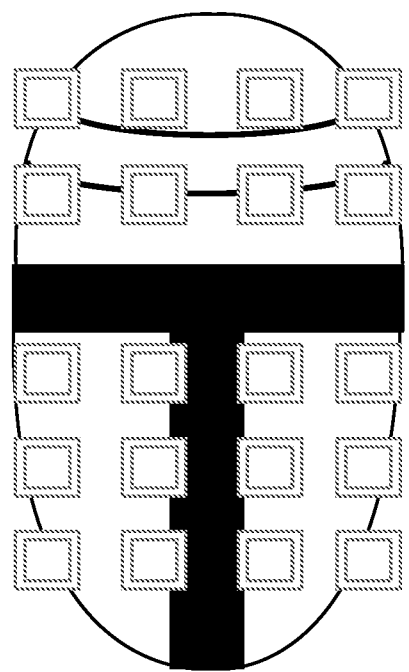

Sensor shielding implemented for each sensor, may include multiple field generating coils situated along multiple dimensions. As shown in FIG. 6, field coils may span in the x direction, marked by dashed lines; span in the y-direction, marked by solid lines; and/or span in the z-direction, as shown by the dotted line. Similarly, the sensor shielding 130 field coils may be implemented over the entire wearable structure. For a helmet wearable structure variation, as shown in FIG. 7, the field coils may be similarly positioned along the entire helmet. Dependent on implementation, as shown in example FIG. 8, the field coils are not required to be orthogonal, and may have more complex positioning geometries to shield the wearable structure. In this example, coverage of different sets of field coils may overlap, but may still sufficiently span the necessary space for proper shielding of the helmet. In another helmet example, as shown in FIG. 9, the field coils may additionally, or alternatively, include multiple smaller coils that span over the surface of the helmet.

The wearable field sensing device may include a power system 150. The power system function to provide power to all necessary system components, i.e. all necessary sensor components and active sensor shielding 140 components. There may be some variations for the power system dependent on the wearable structure 110 and implementation variations. In some preferred variations, the power system 150 includes a portable battery on the wearable structure. The battery may, or may not, be rechargeable. For rechargeable implementations, the battery may be removed for charging, or the power system 150 may have a charging interface, e.g., a USB connection for charging. Additionally, or alternatively, the power system 150 may include other power sources. For example, the power system may comprise capacitors that may be charged (e.g. through a USB connection) on a regular basis for functionality. Alternatively, for a portable cap implementation, the power system, 150 may include solar panel coverings that could charge the system components as necessary.

The wearable field sensing device may include control circuitry 160. The control circuitry 160 functions to control sensor components and other system components, as necessary; and to "process" data acquired by system components. The control circuitry 160 may be directly electrically coupled to other system components (e.g. the wearable structure 110), completely disjoint from other system components, or something in between. In variations, wherein the control circuitry 160 is disjoint, the control circuitry may include wireless communication technology (e.g. IR or Bluetooth), wherein the other system components may connect directly to the control circuitry or connect through a network (e.g. internet). In other variations, wherein the control circuitry 160, is not completely disjoint, the control circuitry 160 may connect to desired components through a wired connection or other means.

The control circuitry 160 may control some and/or all components that require some type of control mechanism. For the helmet example, the control circuitry 160 may control which sensors are active at any one time. Additionally, the control circuitry 160 may be involved in active noise detection and filtering. Active noise detection and filtering may occur with and without sensor shielding 140 components. Through the control circuitry 160, sensors and sensor components may be activated and deactivated as desired. That is, individual sensor components, individual sensors, groups of sensor components, and/or groups of sensors may be activated at any time. Independent function of sensors and sensor components may improve device functionality and/or enable additional functionalities. For example, sets of sensors may be activated in succession such that while sensor nodes from a single sensor, or groups of sensors, are active measuring an EM field while other nearby sensors are inactive. This type of measurement may help reduce noise measured by the activated sensors, by reducing external sensor noise (i.e. cross-talk) during measurements. In some implementations of this example, only certain sensor components may be turned off (e.g. components that emit radio frequency signals). In a second example, sensors may be generally inactive, and are only activated at certain times (at some frequency of activity). This second example may additionally help to reduce power consumption.

The control circuitry 160 may enable multiple operating modes. Operating modes include modes for recording sensor data, controlling sensor activity, and processing sensor data. The control circuitry 160 may additionally or alternatively include other types of operating modes with regards to sensors. The control circuitry 160 may additionally or alternatively include operating modes for non-sensor components. For example, the control circuitry 160 may control/activate: a navigation system (e.g. GPS activation), a monitoring system (e.g. camera activation), an activity tracker (e.g. IMU), etc. Activity of the control circuitry 160, and operating modes, preferably function automatically, but may be activated, deactivated, and/or altered by a user/administrator.

For sensor activity, the control circuitry 160 may enable sophisticated operating modes based on "low-power" modes, to conserve energy; noise reduction modes, that reduce noise; optimization modes, to improve sensor functionality, recursive modes to improve performance; and any other desired type of modes related to sensor activity. In some preferred variations, the system may additionally include operating mode specific components to optimize specific types of processor system sensor activity nodes. For example, for a system with desired low power consumption activity, the system may include a low power sensor, as the sensor device shown in FIG. 14, to be implemented in conjunction with a low power operating mode.

The control circuitry 160, preferably includes processing modes. Processing modes function to process sensor data and determine the source of the EM field in the user tissue. That is, from the sensor node data received, the processing mode determines the EM field profile in the user/patient tissue. The processing mode may additionally or alternatively localize the source of measured activity. Localization may be used to determine which sensors are appropriate positions for more detailed activity detection. In preferred variations, the control circuitry 160 has at least two processing modes: a spatial averaging mode and an inverse solution mode. The control circuitry 160 may additionally or alternatively have other processing modes. Processing may function independently and/or in simultaneously.

The inverse solution mode preferably takes all sensor node data, and through the array of all available active sensor nodes, finds a solution to the inverse problem to determine the EM field profile. The control circuitry 160 may solve the inverse problem using any desired numerical method (e.g. using a Bayesian approach or least-squares). As for many implementations of the system, wherein the number of sensor nodes is on the order of ~10000, real-time calculation of the EM field profile may be limiting factor of the inverse solution. Additionally, noise may be severe limiting factor in direct implementation of the inverse solution mode.

Additionally, the control circuitry 160 may include a spatial averaging mode. The spatial averaging mode preferably functions as a course graining implementation of the sensor data. In the spatial averaging mode, sensor nodes are grouped into clusters, wherein the sensor data is spatially averaged over each cluster. Course graining preferably reduces system noise and preferably simplifies the inverse problem by order of the cluster size, while sacrificing precision of the EM field profile. Dependent on the time scale of the evolution of the EM field, and other desired factors, the control circuitry 160 may determine the level of course graining to be implemented for course graining. For example, the control circuitry 160 may not implement a spatial averaging mode if the EM field evolves on the order of hours and is for a small heart patch comprising 500 sensor nodes; while alternatively, the control circuitry 160 may implement a spatial averaging of cluster size 100 (e.g. for 10000 sensor nodes of a helmet) for an EM field that evolves on the order of milliseconds. In some implementations, a user/administrator may set the level of spatial averaging.

The control circuitry 160, may additionally include an optimization mode. Through the optimization mode, the system may improve the signal to noise ratio (SNR), optimize field calculations, and/or speed up field calculations. Optimization modes may be methods that improve results over iterations of calculations. Through initial calculations, preferably using a course grained spatial averaging mode, the control circuitry 160 may determine the sources and general profile of the EM field. In the optimization mode, through iterative calculations, the control circuitry 160, may deactivate sensor nodes not significant (e.g. far from the source) to simplify and improve the field calculation, thereby reducing the number of sensor nodes utilized for an implementation. This in turn may reduce the level of required course graining (e.g. increasing precision) and reducing system noise from unnecessary sensor nodes.

The control circuitry 160, preferably includes a noise reduction mode of operation. The noise reduction mode preferably functions to reduce noise. The noise reduction mode preferably includes implementations to reduce both external noise (e.g., earth's magnetic field) and internal noise (e.g., system non-linearities). In one implementation, external noise may be reduced by subtracting the external field measured by the ambient sensor array 130. Additionally, field coil sensor shielding 140 may be activated to reduce or cancel out measured external fields. In another implementation, internal noise may be reduced by spatial averaging. In a third implementation, inaccuracies (e.g., inaccuracies due to non-linearities) may be reduced by normalizing the detected field to a linear regime of the sensor (e.g. near zero), thereby reducing the noise of each sensor. Additionally, with this second implementation, the system may include sensors that comprise linearizing circuitry. In a third implementation to reduce noise, the control circuitry 160 may gather data from spatially clumped groups of sensor nodes at one time, while turning off sensor nodes near the spatially clumped group; thereby reducing sensor noise.

The control circuitry 160, preferably includes a low power operating mode. The low power operating mode may function to minimize the power usage of the system during operation. Low power operation may be particularly useful for extended use monitoring, particularly in implementations outside of a lab or clinic and other places far from an accessible power source. During low power operation, the control circuitry 160 preferably turns off sensors and other system components that are not necessary for function at a given time and may limit the rate of data acquisition as desired (e.g. one sensor measurement per minute). For example, the control circuitry 160, may turn off all but only a subset of the sensors (e.g. one active sensor) from the biological sensor array 120 are active until biological activity is detected. Once biological activity is detected, the control circuitry, may then activate some and/or all of the biological sensor array 120 and/or the ambient sensor array 130. Low power mode may preferably function in conjunction with other operating modes. Additionally, in some implementations of the lower power mode, sensors may comprise low power sensor devices.

Low power operation may occur in different phases of operation, and may differ in the type of operation. In some variations, the system may include an EM-localization low power operating mode. The EM-localization low power operating mode may function to identify the source of an EM field (e.g. identifying the locus of some brain activity). In a helmet implementation of the wearable sensor device, the low power operating mode may comprise the control circuitry 160 activating a limited number of sensors over the entire span of the helmet (e.g. one in every four sensors in each region of the helmet may be activated). In this manner, the localization low power operating mode may utilize a "mesh" of sensors to find the signal locus. Dependent on the desired implementation and limited by the actual sensor density of the helmet, the mesh size may be increased or decreased as desired.

The system may also include a monitoring low power operating mode. The system may start or switch to a monitoring low power mode after some initial operation. For example, in one implementation of a helmet sensor device, sensors may be initially active to identify the locus of a certain type of brain activity (either in a regular or a low operating mode). Once the brain activity has been identified and the source located, the system may then switch to a monitoring low power mode, wherein sensors closest to the locus stay continuously active while other sensors are turned off. Single, multiple, or varying regions may be monitored in this manner simultaneously or in succession. Once definite activity has been identified, the control circuitry may then exit low power mode and enable full monitoring of the brain activity.

In some variations, the system can be used as an input device so that sensed activity can be used as a form of input to a connected device such as a computer. In this manner the system may provide an input as part of a BCI, wherein the system input device is integrated with other component outputs (e.g. as part of a VR flight simulator training application). In one variation, the sensed activity can be communicated as raw activity data (possibly preprocessed for noise removal and/or for other enhancements). In one example, the system may be used for medical research and/or medical imaging. Additionally, or alternatively, the output signal from the system can be activity/event classification or characterization. Machine learning models, heuristic models, and/or other analysis processes may be used to detect and classify different activity states from the sensed activity. This may be used to detect user intention and thoughts to control other connected devices. The input may be used as a form of direct user input but may alternatively be used as a form of user state input. Analysis of the sensor signal can be used to detect mental states such as attention, emotions, tired/distracted, stress, relaxation, focus, and/or other states. The system may also be able to detect abnormal states such as seizure or an oncoming seizure. When applied to sleep monitoring it may be used to track duration of different stages of sleep.

In some variations, the system may additionally include a computer system integration, wherein external data inputs from one or more external computer systems may be used in coordination with the operation of the wearable field sensing device. The computer system integration can be an application, computer service, operating system, or other suitable specialized configuration of a computer-readable medium (e.g., a non-transitory computer-readable medium) that includes instructions when executed cause a computer system to perform various operations. These operations may involve dynamic control of the wearable field sensing device in response to data input from one or more external computer systems. For example, the biological sensor array may alter sensing operation mode (e.g., changing from low power mode to a higher power mode) in response to data input from one or more external computer systems. This may as part of BCI to trigger responsive sensing of brain activity in response to different states in a computer system. Different localized regions of the biological sensor array may be activated depending on the requirements. For example, monitoring for different brain activity associated with particular motor activities may be used when the computer system wants to monitor for a particular action. In another example, monitoring for different brain activity associated with visual processing regions of the brain when monitoring for visual activity.

The operations may alternatively involve dynamic control of the one or more external computer systems in response to the wearable field sensing device. The measured signals from the wearable field sensing device may processed and/or used in altering operating state of a connected computer system. This may be used to use the wearable field sensing device as a user interface input device for a computer.

In one sample example for the wearable field sensing device, the system comprises a wearable structure, comprising a portable cap fitted to a user head; a biological sensor array, situated on the portable cap such that each sensor is adjacent to the user head once the portable cap is worn, spans at least one distinct region of the user head of a user, for field measurements in the at least one distinct region, comprises at least 100 sensors per distinct region, and wherein each sensor comprises an integrated circuit comprising an acoustically driven ferromagnetic resonance (ADFMR) sensor, configured to measure the EM fields on and within the head of the user; an ambient sensor array, comprising: an array of ADFMR sensors situated on the portable cap configured to measure ambient EM fields in proximity of the portable cap; sensor shielding, comprising a set of field coils situated on the portable cap and enabled to generate magnetic fields on and around the portable cap; a power system, comprising a battery situated on the portable cap; and a control circuitry, electrically coupled to the system, enabling the system to function in a low power operating mode, comprising operation of a subset of the biological sensor array, and enabling the system to function in a noise reduction operating mode, wherein the noise reduction operating mode comprises activating the set of field coils to cancel ambient EM fields measured by the ambient sensor array.

3. ADFMR Sensor

Figure 10:
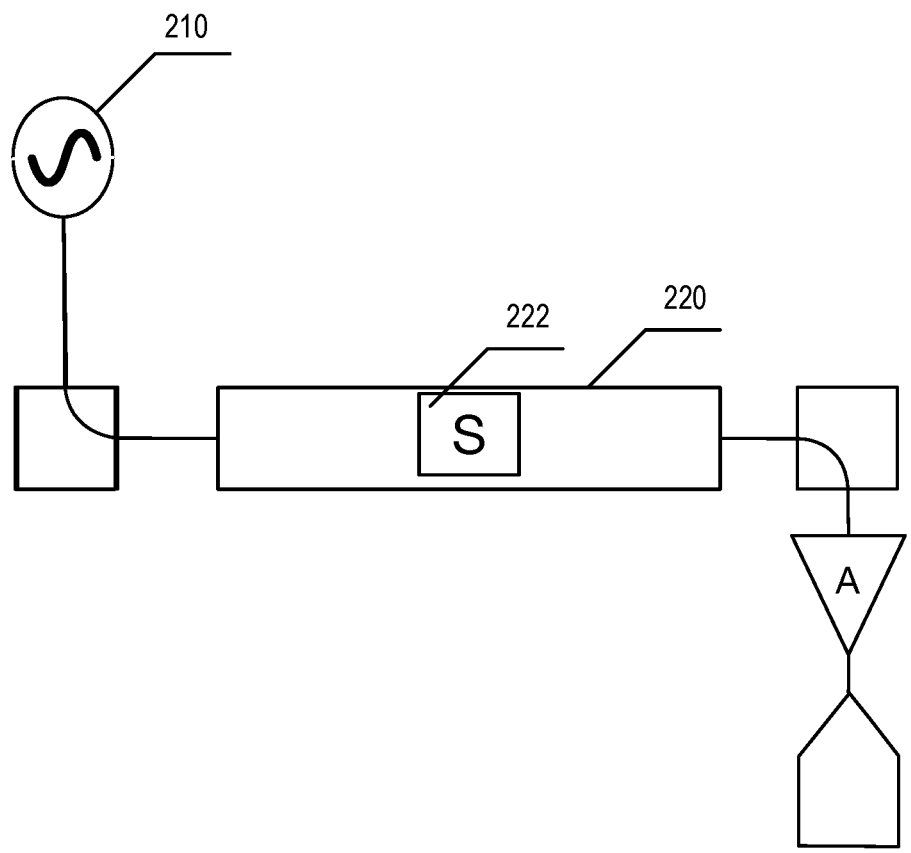

The ADFMR sensor may comprise an acoustically driven ferromagnetic resonance (ADFMR) sensor device, as described in U.S. patent application Ser. No. 17/120,907, filed on 14 Dec. 2020 and which is hereby incorporated in its entirety by this reference. As shown in FIG. 10, an acoustically driven ferromagnetic resonance (ADFMR) based sensor includes: a power source 210, that provides an electrical signal to power the system; and an ADFMR circuit 220, i.e. a first "test" circuit, sensitive to electromagnetic fields, wherein the ADFMR circuit comprises an ADFMR device 222, and a detector circuit comprising an analog to digital converter. The ADFMR sensor functions as the ADFMR sensor described as part of the biological sensor array and ambient field array to detect and measure external electromagnetic (EM) fields by measuring a perturbation of the electrical signal through the ADFMR circuit due to the EM fields. In some preferred embodiments, the ADFMR sensor may include at least one additional circuit (e.g. an additional test circuit, or a reference circuit), wherein the system further includes at least one power splitter 232, wherein the power splitter splits the electric signal to the at least one circuit; and at least one power combiner 234, wherein the power combiner combines the potentially perturbed electric signal output from the ADFMR circuit 220 with other electrical signals.

Figure 11:
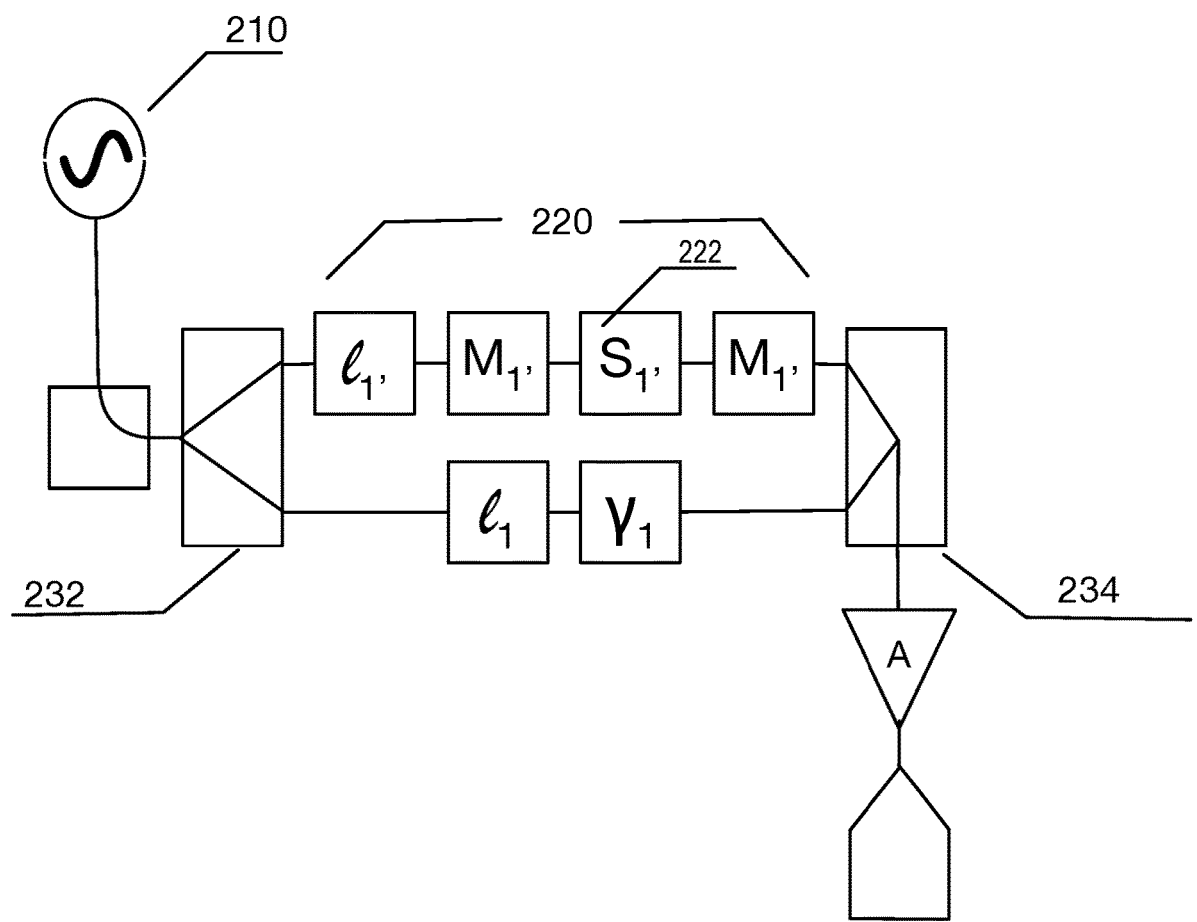
FIG. 11 is a schematic representation of an interferometer ADFMR sensor.

In some variations that include at least one additional circuit, as shown in FIG. 11, the at least one additional circuit comprises a first signal processing circuit, wherein the first signal processing circuit is situated parallel to the ADFMR circuit 220 and functions as a "reference" to the ADFMR circuit. This system variation, i.e. interferometer variation, functions to detect and measure external electromagnetic (EM) fields by comparison of a perturbation of the electrical signal through the ADFMR circuit 120, as compared to the unperturbed electrical signal through the first signal processing circuit, i.e. a first reference circuit. That is, in the interferometer variations of the system, the power signal through the ADFMR circuit 220 is perturbed by an external field that is then interfered with an unperturbed reference signal from the reference circuit. The interference (e.g., destructive interference) profile between the test signal and the reference signal, may then be used by the detector circuit to determine the field strength.

Figure 12:
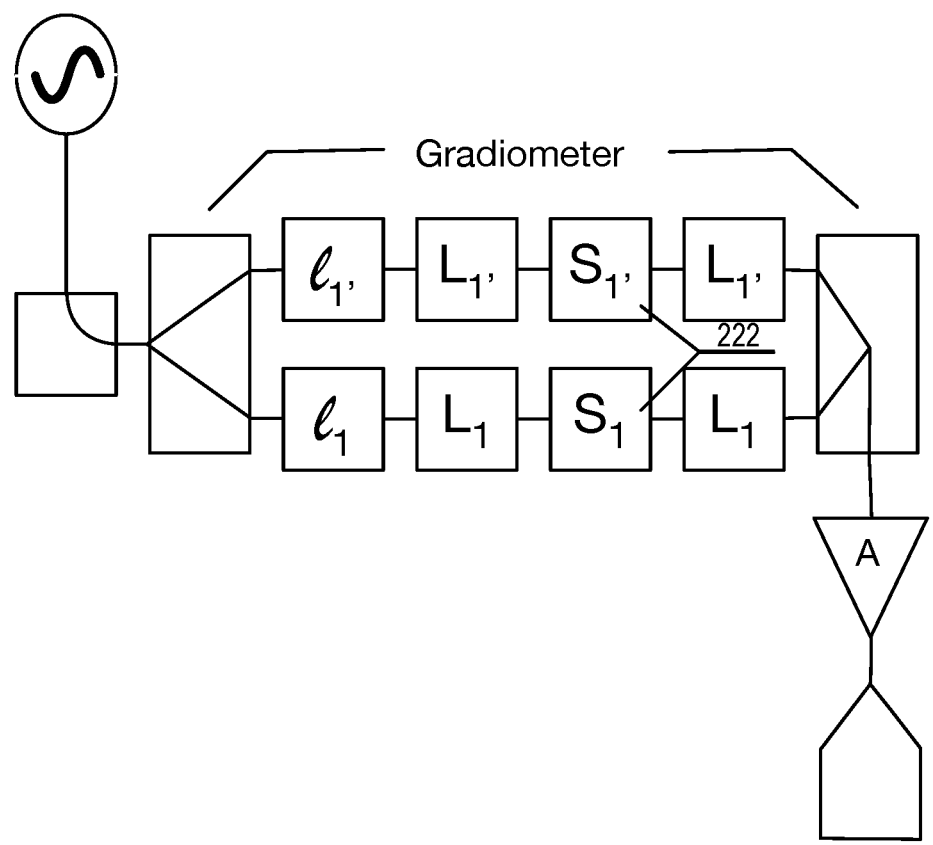
FIG. 12 is a schematic representation of a one-dimensional gradiometer ADFMR sensor.

In another variation, as shown in FIG. 12, the system may function to measure the change (i.e. gradient) of external EM fields, i.e. function as a gradiometer. In gradiometer variations, the at least one circuit may comprise an additional ADFMR circuit 220, i.e. a second test circuit that is sensitive to EM fields. In this variation, the difference in measurement between the first test circuit and the second test circuit may be used to determine the gradient of the EM field. That is, in the gradiometer variations of the system, the power signal through both ADFMR circuits 220 are perturbed by the external field. By taking into account the positional dependence of the two circuits, measurement of the gradient of the field can be enabled through interference (e.g., destructive interference) measurements between the two signals.

In many variations, the system may additionally, or alternatively, include subcomponents to increase and/or modify system capability. Examples include: additional ADFMR devices 222 (e.g. enabling multi-dimensional field measurements), amplifiers (e.g. to amplify the power/electrical signal), filters (e.g. to reduce internal and background noise), matching networks (e.g. to match the signal power between parallel circuits), attenuators, phase shifters (e.g. to alter interference patterns between test and reference signal), mixers (e.g. to mix signal frequency), magnetic field coils (e.g. to shift the signal band), and any other desired components. Examples of potential system subcomponents include: signal amplifiers (A), bandpass filters (F), attenuators (l), inductors (L), phase shifters (γ), couplers (c), mixers (X), matching networks (M), analog to digital converters (ADC), digital to analog converters (DAC), and comparators (≥), logic circuits, and field coils. The system may include any other desired components as applicable. FIG. 13 includes a glossary of terms and symbols of subcomponents implemented in some variations of the system.

These subcomponents may enable many additional variations. For example, the system may comprise: variations optimized for low energy consumption, as shown in one example in FIG. 14; variations to reduce noise, as shown in one example in FIG. 15 example; and variations that optimize the sensitivity and/or operating range of the system, as shown in one example in FIG. 16. The system may additionally, or alternatively, comprise any combination or additional variation, as desired.

The system may include circuits and circuit segments, parallel or in series, as part of the system. These circuits may contain any circuit subcomponents (e.g. the aforementioned subcomponents), as desired for functionality. As used in this section, the term "circuit" will be used generally, to refer to either an entire circuit, or a circuit segment. That is, a circuit will not necessarily form a closed loop per se, but with the combination of additional circuits, that may or may not be explicitly presented here, the circuit may function as part of a closed loop.

Figure 17:
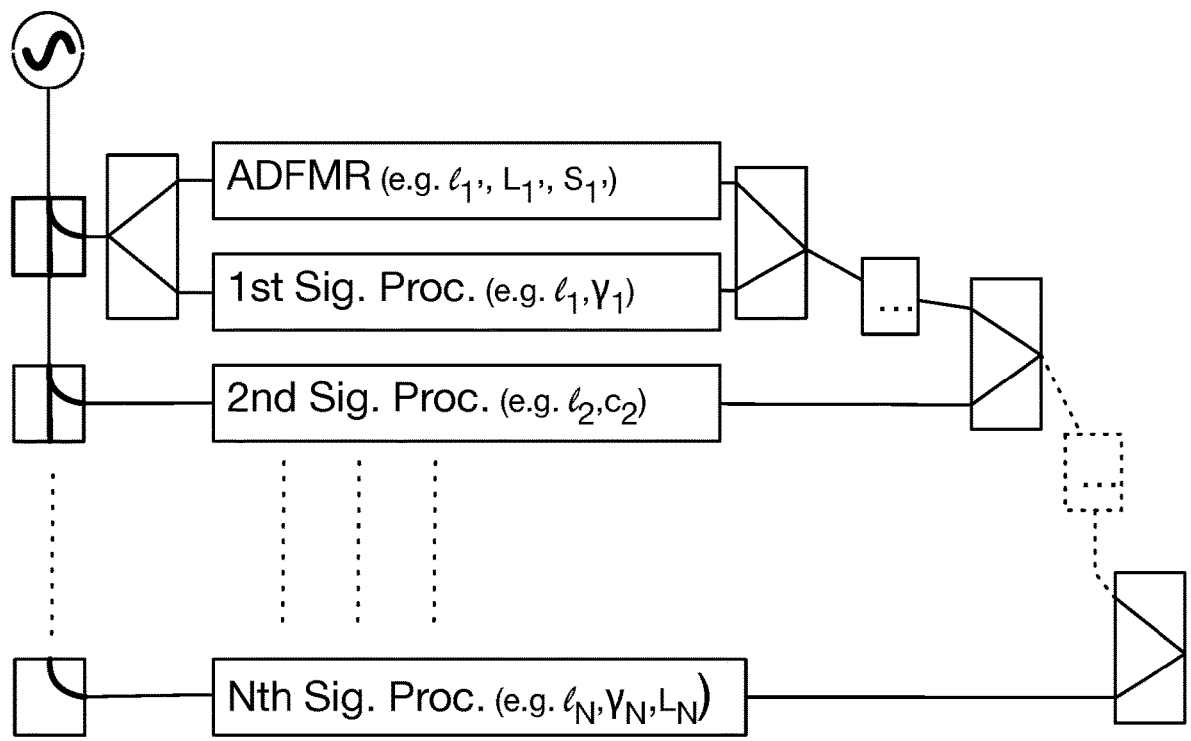
FIG. 17 is a general circuit schematic representation of an interferometer ADFMR sensor.
Figure 18:
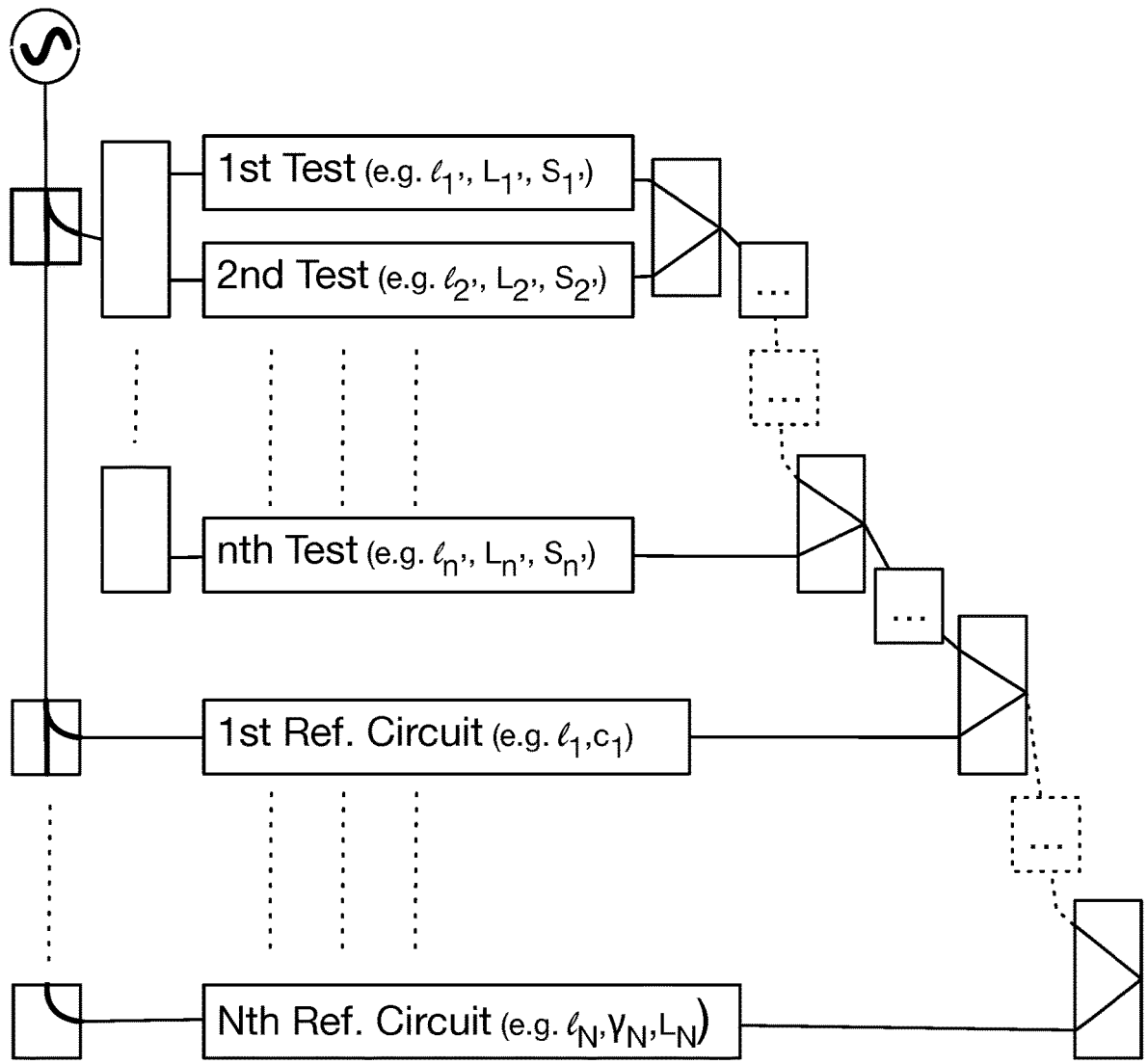
FIG. 18 is a general circuit schematic representation of the ADFMR sensor.

As shown in FIG. 17 and FIG. 18, numbering for circuits refer to the number of test circuits (shown with primed subscript numbers), circuits that include an ADFMR device subcomponent; and signal processing circuits (shown with subscript numbers). Test circuits may also be referred to as ADFMR circuits or sensor circuits. Additionally, the first test circuit may also be referred to without a numbering, e.g. the test circuit, or the ADFMR circuit. Although circuits are shown numbered only in parallel in the figures, variations of the system may include that test circuits and/or signal processing circuits in other non-parallel configurations within the circuit.

In a general circuit layout of the system, as shown in FIG. 18, the system may comprise "n" test circuits and "N" signal processing circuits, wherein n and N are arbitrary whole numbers determined by the specific implementation. Circuit subcomponents, i.e. components on a specific circuit, may be referred to with a subscript referring to the circuit number, wherein primed subscripts will be used for test circuit subcomponents (e.g. $L_{2'}$ refers to an inductor on a second test circuit) and non-primed subscripts will be used for signal processing circuit subcomponents (e.g. $L_2$ refers to an inductor on a second signal processing circuit). In some variations, certain subcomponents may appear in regions where it is not clear which circuit these components belong to. These subcomponents may be included without any subscript, or may include a subscript to connect it with a desired circuit (e.g. when the subcomponent has a complementary functionality with the desired circuit).

As part of a circuit designation, circuit subcomponents may be described as upstream or downstream in relation to each other. Herein, "upstream" and "downstream" are used to refer to the direction of power traveling through the circuit. That is, a subcomponent 'A' downstream from subcomponent 'B' would refer to a positionality where the power travels from subcomponent 'B' to subcomponent 'A', with or without other components in between. A subcomponent 'A' upstream from subcomponent 'B' would refer to a positionality where the power travels from subcomponent 'A' to subcomponent 'B', with or without other components in between.

A system may include a power source 210. The power source functions as an energy source, providing an electrical signal to the system. In some variations, the power source 110 is an electronic oscillator. The electronic oscillator functions to provide the system with an oscillating voltage, i.e. an alternating current (AC) power signal, wherein the power from the oscillator is used to activate the sensor circuit. Alternatively, other types of currents may be used, e.g. direct current (DC).

In some variations, the electronic oscillator is a voltage-controlled oscillator (VCO). Preferably the frequency of the oscillator is in the order of gigahertz. More preferably –2 GHz. High frequency pulsing of the oscillator may enable fast turn-on and turn-off times of the sensor. Fast turn-on/turn-off times may be on the order of microseconds or faster. As the ADFMR device 222 may function with MHz oscillations, the oscillator may alternatively be in any range that enables ADFMR functionality, that is in the order of MHz to GHz.

The system may include at least one ADFMR circuit 220. The ADFMR circuit 220 functions as a "test" circuit that includes an ADFMR device which enables sensor activity for the system. The ADFMR circuit 220 may also be referred to as a sensor circuit or a test circuit. Dependent on the variation, the system may include one, or multiple, ADFMR circuits 220; wherein each ADFMR circuit may share ADFMR devices 222 between them, have a single ADFMR device, or have multiple ADFMR devices. In some variations, the system may include a set of ADFMR circuits. Multiple ADFMR circuits 220 may be used for gradient field measurements, multidimensional field measurements, and/or to improve field measurement precision (e.g. through overlapping measurements). ADFMR circuits 220 are positioned downstream of the power source 210, such that the electrical signal provided by the power source may be implemented as a test signal along the ADFMR circuits.

Figure 19:
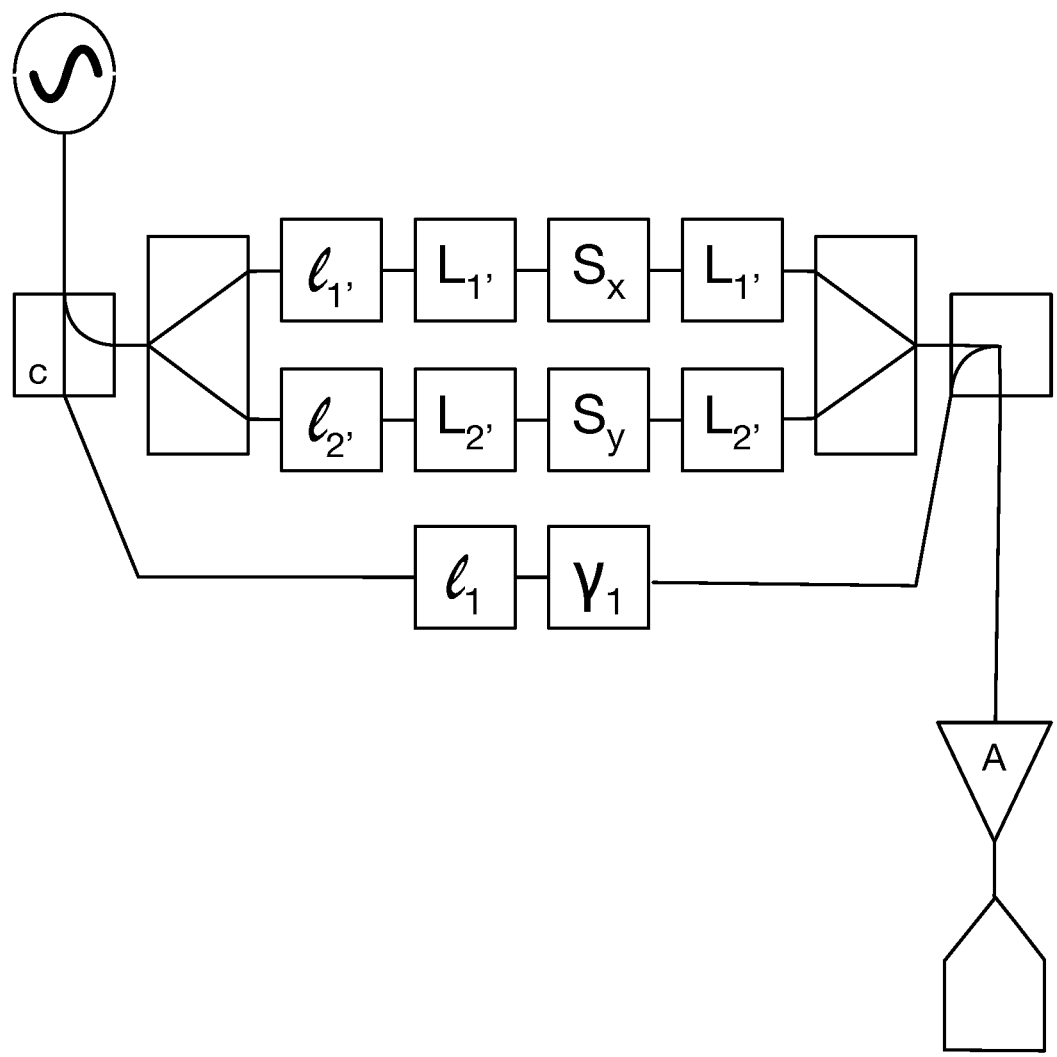
FIG. 19 is a schematic representation of a two test circuit, two-dimensional interferometer.
Figure 20:
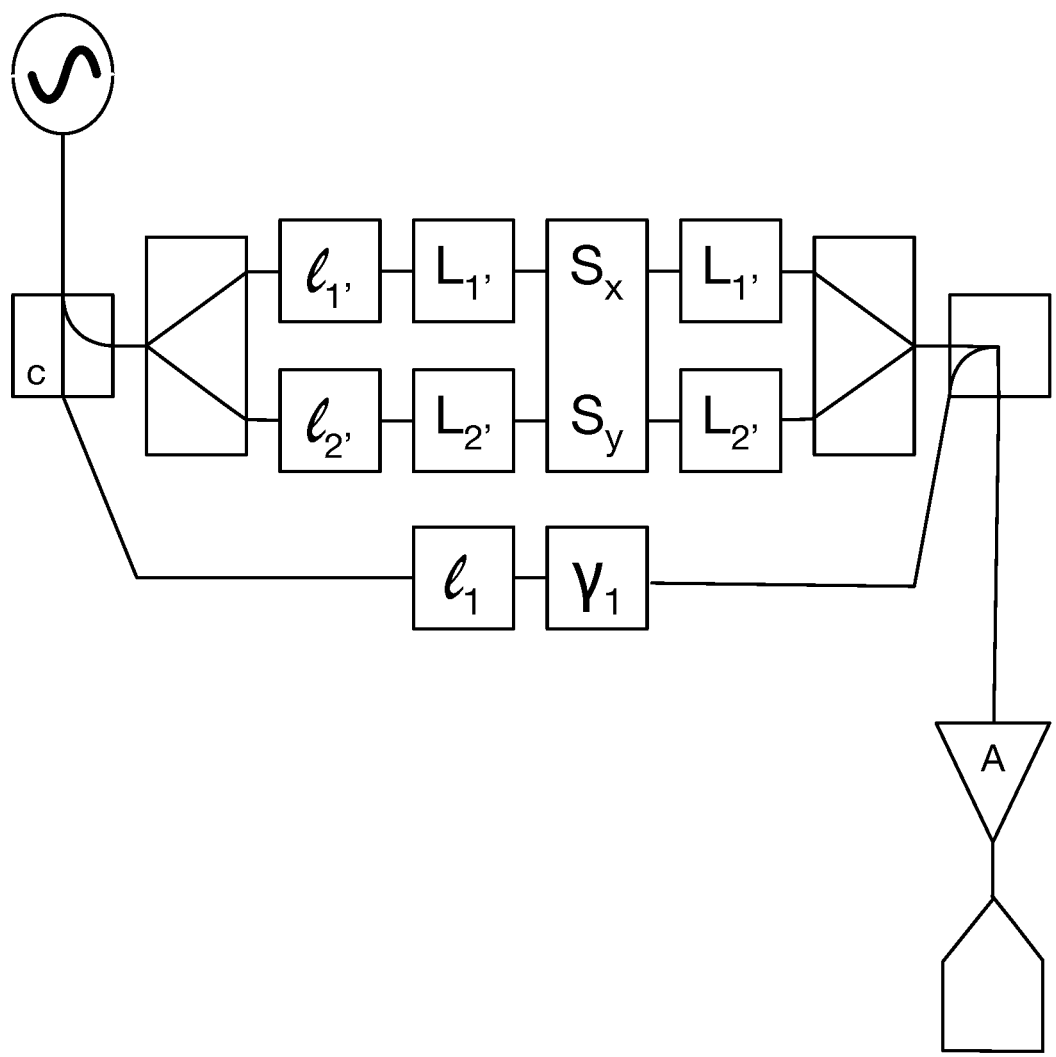
FIG. 20 is a second schematic representation of a two test circuit, two-dimensional interferometer.

In some variations, the system may comprise multiple ADFMR devices 122, distributed on ADFMR circuits 220, In one variation, multiple ADFMR circuits 120 measuring one, or multiple, dimensions may be implemented on a single chip, much similar to the layout as shown in FIG. 19 or FIG. 20. Dependent on the desired implementation, each dimensional functionality may be activated or deactivated.

Figure 21:
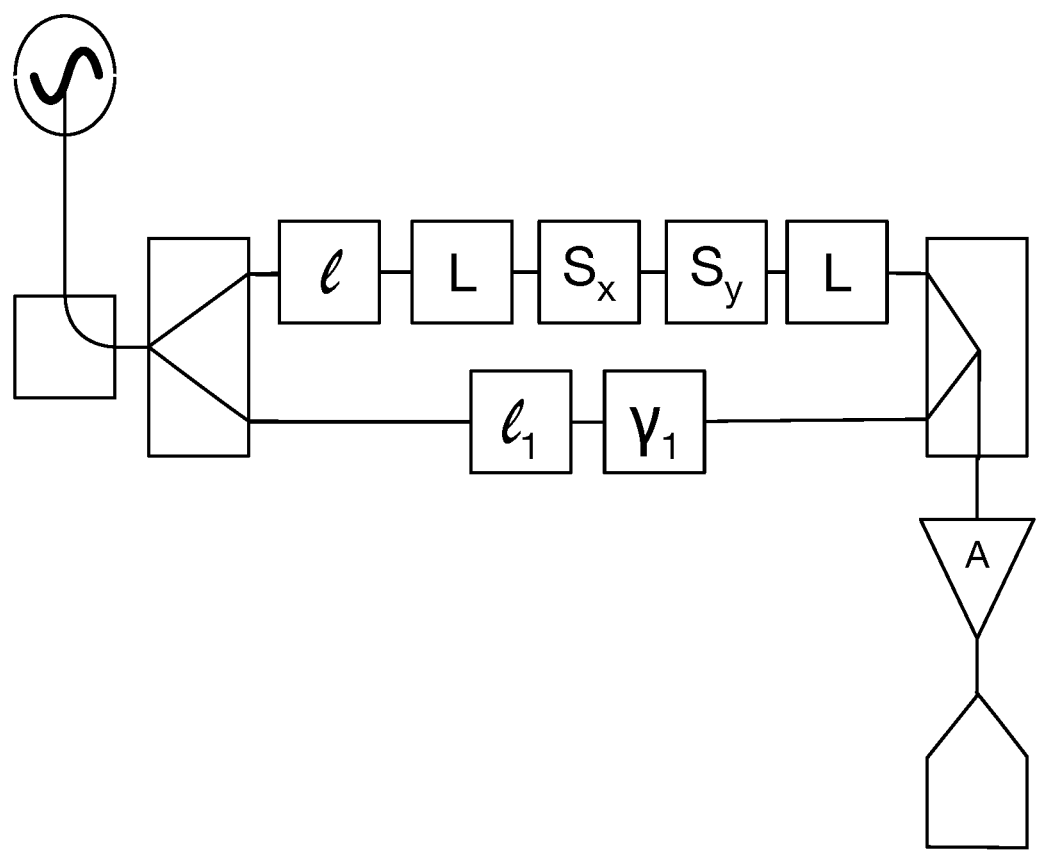
FIG. 21 is a schematic representation of a one test circuit, two-dimensional interferometer.

In one variation, a single ADMR circuit 220 measuring one, some, or all desired dimensionalities may be implemented on a single chip, much similar to the layout as shown in FIG. 21. Dependent on the desired implementation, each dimensional functionality may be activated or deactivated.

The ADFMR device 222 is preferably a component of the system, and additionally, a subcomponent of the ADFMR circuit 220. The ADFMR device 222 functions as a device that "measures" EM fields by enabling modification of a radio frequency (RF) carrier signal (i.e. the test signal) using acoustically driven magnetic resonance. In many variations, the magnetic resonance is implemented with a ferromagnetic (i.e. ferromagnetic resonance), but may be implemented with any magnetic material. Examples of other types of magnetic material include: anti-ferromagnets, ferrimagnets, etc. That is, although the device is referred to as an ADFMR device 222, the ADFMR device may in actually be a, e.g., ferrimagnetic resonance device. The ADFMR device 222 may include: at least one acoustic transducer, that generates and/or absorbs acoustic waves; an acoustic resonator, that provides a medium for acoustic wave propagation; and a magnetic material, that perturbs the acoustic wave due to EM fields using magnetic resonance.

The ADFMR device 222 preferably includes an acoustic transducer. The acoustic transducer functions to convert the test signal to an acoustic wave, and/or convert the acoustic wave to an RF signal (e.g. an altered test signal). The acoustic transducer functions to generate and/or absorb acoustic waves (or pressure waves), from an electrical signal, that propagate along the acoustic resonator (e.g. piezoelectric substrate).

Preferably, the acoustic transducers are implemented in pairs, wherein one transducer generates the acoustic wave that then propagates to the other acoustic resonator that is then absorbed by the second transducer. That is, a first acoustic transducer converts the test signal traveling through the ADFMR circuit 220 into an acoustic wave; wherein the acoustic wave propagates in, or along, the ADFMR device 222 to a second acoustic transducer, which then converts the acoustic wave to an electrical signal. Alternatively, a single acoustic transducer may both convert the RF test signal to an acoustic wave, and the acoustic wave back into an RF signal. For example, an electrical signal may be converted into an acoustic wave by an acoustic transducer, the acoustic wave propagates out and is then reflected back to the acoustic transducer, which then converts the acoustic wave back into an electrical signal. In other examples, multiple acoustic transducers may be implemented both to generate and to absorb the acoustic waves. That is, multiple acoustic transducers may be implemented per ADFMR device 122, wherein a single, or multiple, RF signals may be converted to acoustic waves and/or acoustic waves converted to RF signals; once, or multiple times.

The acoustic transducer preferably generates an acoustic wave appropriate to the type of ADFMR device 222. Examples of generated acoustic may include: surface acoustic waves (SAWs), bulk acoustic waves (BAWs), and lamb waves. The specific acoustic transducer may be implementation specific. The type of acoustic transducer may be dependent on the electrical signal (e.g. signal frequency, signal power), and/or the type of acoustic wave generated (e.g. surface acoustic, bulk acoustic waves). For example, in variations wherein the system uses lamb waves, the acoustic transducer may comprise of electromagnet-acoustic transducers (EMAT). In variations wherein the system uses SAWs, the acoustic transducer may comprise interdigital transducers (IDTs). Alternatively, other types of transducers (e.g. film bulk acoustic resonators, high-overtone bulk acoustic resonators) may be implemented that either generate SAWs or other types of acoustic waves. The acoustic wave is preferably generated at, or near, the resonance frequency of the ferromagnet. The acoustic wave is preferably propagated in, or along, the acoustic resonator through the ferromagnet. Thus, the acoustic wave may enable the ferromagnet to function at, or near, resonance.

Figure 22:
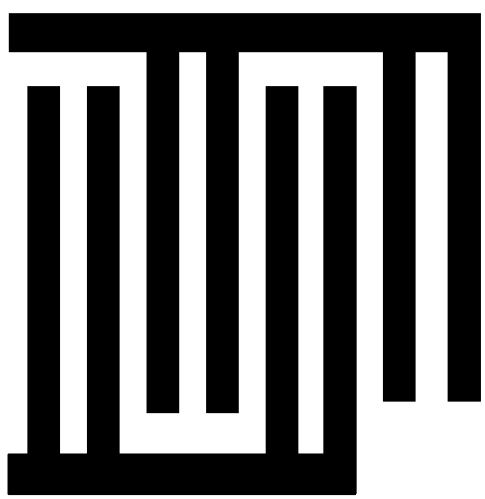
FIG. 22 is a sample illustration of an interdigitated transducer (IDT)

In some variations wherein the system uses SAWs, the acoustic transducer may comprise an IDT. The IDT may function to generate a SAW from an electrical signal (or generate an electrical signal from a SAW) using the piezo-electric effect. The IDT is a device comprising of interlocking comb-shaped arrays of metallic electrodes, forming a periodic structure, positioned on a piezoelectric substrate (e.g. quartz, lithium niobate). The IDT may have any desired configuration/shape. One example IDT configuration is shown in FIG. 22. For the pairs of IDTs, preferably one functions as an input IDT and one functions as an output IDT. The input IDT may convert a radio frequency (RF) electrical signal to a surface acoustic wave (SAW) using the piezo-electric effect. The output IDT functions by absorbing the SAW and converting it back to an electrical signal.

The ADFMR device 222 may include an acoustic resonator. The acoustic resonator functions as a medium to enable propagation of acoustic waves. The acoustic resonator may enable wave propagation through a volume (e.g. BAWs), along the surface of a medium (e.g. SAWs), through the cavity of a medium (e.g. sound waves propagating through an air cavity of the acoustic resonator). The acoustic resonator may be composed of any material that enables the desired type of acoustic wave propagation. In some variations the acoustic resonator is composed of a piezoelectric substrate (e.g. quartz). In some variations, the acoustic resonator may comprise the main "body" of the ADFMR device 222, wherein all other components are situated on, or around, the acoustic resonator.

In some variations, the acoustic resonator is a piezoelectric substrate. The piezoelectric substrate enables formation and propagation of acoustic waves by the piezoelectric effect. The piezoelectric substrate may be composed of any desired piezoelectric compound (e.g. most crystal or ceramic compounds). In one preferred variation a Y-cut lithium niobate substrate is used as the piezoelectric substrate. In some variations that include two acoustic transducers, the length of space between the two acoustic transducers (i.e. delay line) is 1-3 mm. In one example, a piezoelectric substrate (e.g. zinc-oxide) is deposited underneath or above the two IDTs on the ADFMR base (e.g. diamond base material).

The ADFMR device 222 may include a magnetic material, preferably a magnetostrictive material. The magnetostrictive property may enable the magnetic material to convert strain into a change in magnetization, or enable the conversion of a change in magnetization into strain. The only limitation on the magnetic material is that the magnetic material may achieve resonance on a macroscopic scale (i.e. resonance beyond the excitation of individual molecules and/or atoms). Examples of magnetic material include, ferromagnets, ferrimagnets, anti-ferromagnets, paramagnets, diamagnets, etc. In some variations, the magnetic material may comprise a ferromagnet, and/or a ferromagnetic mixture. The magnetic material functions to absorb acoustic waves, wherein at resonance the absorption is very sensitive to magnetic fields. Preferably, the magnetic material is positioned in the path of the acoustic wave (along the delay line), such that the local magnetic field sets the magnetic material's resonant frequency to, or close to, the acoustic wave frequency—thereby enabling the magnetic material to effectively absorb the acoustic wave and thus change the propagating acoustic wave with respect to the magnitude of the field. In preferred variations, the ferromagnet is laid in between the two acoustic resonators (e.g. as a magnetic film), wherein the thickness and length of the magnetic material plays a significant role in absorption, thus the magnetic material may be of varying thickness and be of different length dependent on implementation. For ferromagnetic variations, examples of implemented types of ferromagnets include iron, nickel, and cobalt, but may be any suitable type of ferromagnet. In some variations, the system may be implemented with other magnetic materials, for example: paramagnets, diamagnets, ferrimagnets, antiferromagnets, or any combinations of these materials. Similar to the ferromagnet variation, the magnetic material may be implemented at or near resonance to absorb magnetic fields.

In some variations, the ferromagnetic has a spatial orientation. That is, the ferromagnetic may be built and oriented such that EM fields with one spatial orientation (e.g. x-direction) may affect the interaction between the magnet and the acoustic wave, wherein fields from other orientations may leave the ferromagnet unaffected. In this manner, dependent on implemented ferromagnet, the ferromagnet (and thus the ADFMR device 222) may be sensitive to one, two, or three spatial dimensions.

In some variations, the ADFMR device 222 may include a signal detector. The signal detector functions to measure the output power signal from the ADFMR device 222. Since the output power signal may have been perturbed by the applied field, the output power signal may be used to determine the field strength. The signal detector may additionally include noise reduction functionalities. In one variation, the signal detector may perform a Fourier transform to separate the desired output signal from other extraneous Electromagnetic (EM) waves. For example, an input acoustic transducer may additionally generate extraneous EM waves. The signal detector may perform a Fast Fourier Transform to isolate and remove these extraneous waves from the desired signal. Due to the time delay of acoustic wave propagation, as compared to EM wave propagation, other time dependent methods may be used to separate acoustic waves from EM waves. For example, in one implementation, the electronic oscillator may be cycled on and off for fixed periods of time, enabling measurement of the propagating acoustic waves during the electronic oscillator off cycle, thus potentially removing undesired signals.

Figure 23:
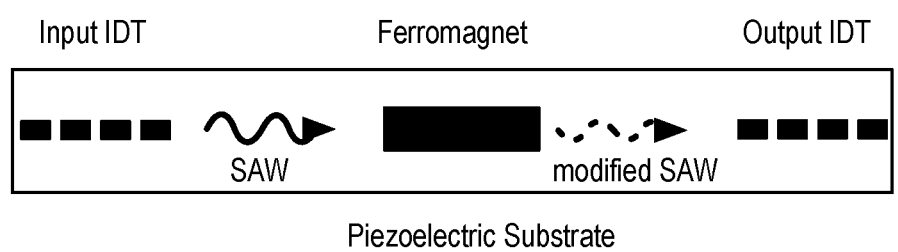
FIG. 23 is a schematic representation of a surface acoustic wave (SAW) device.
Figure 24:
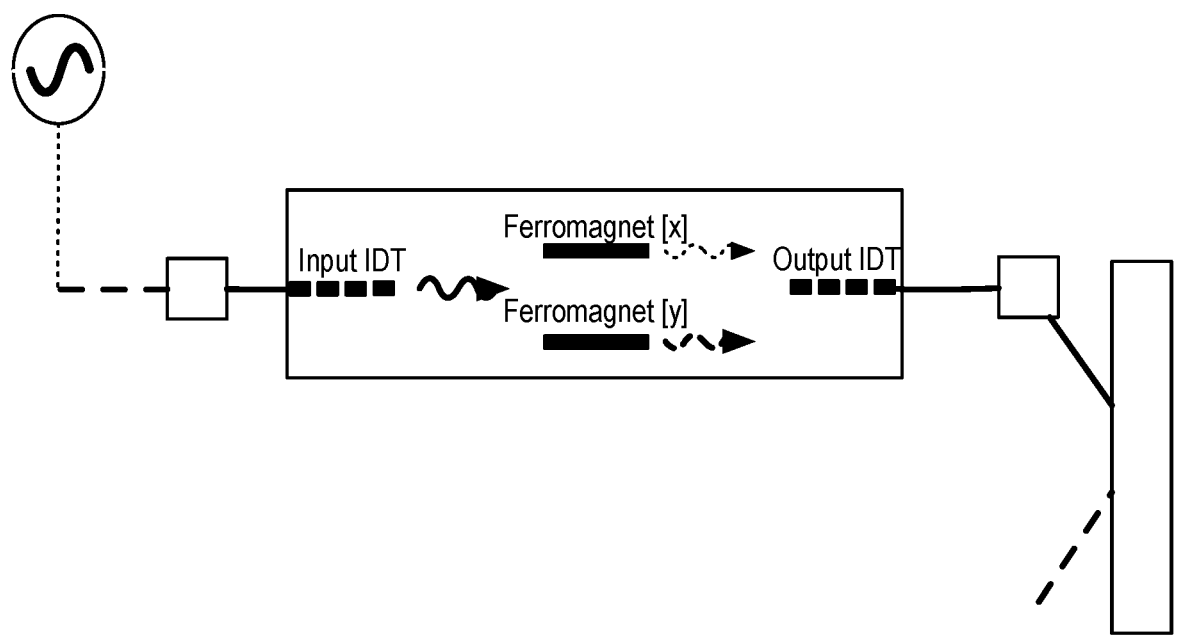
FIG. 24-28 are schematic representations of alternate variations of the SAW device.
Figure 25:
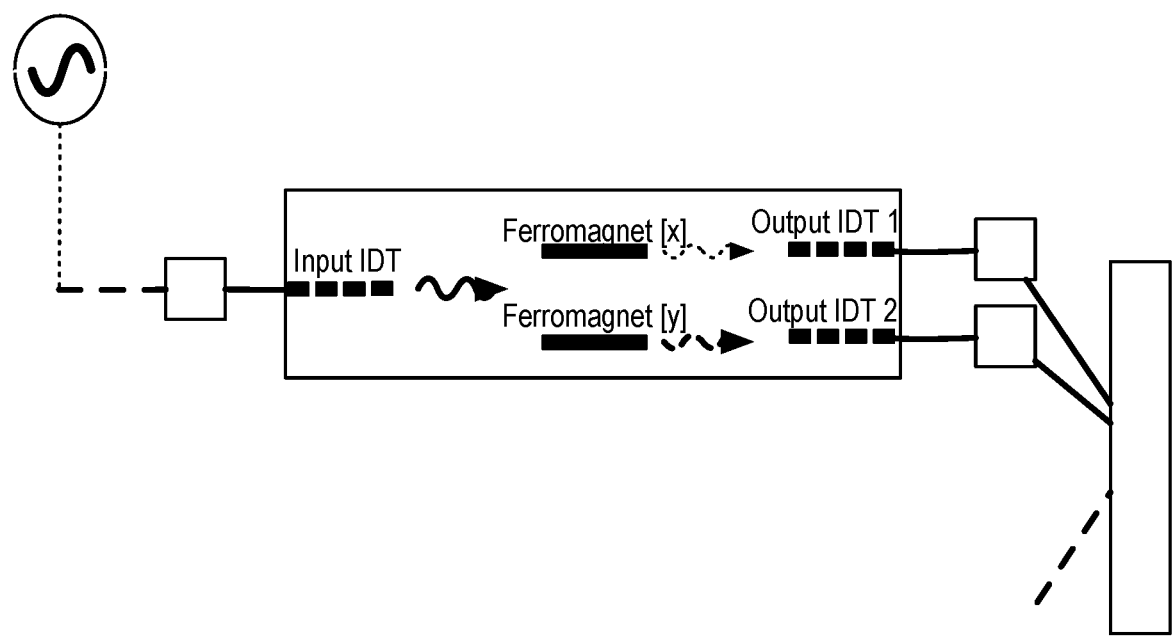
Figure 26:
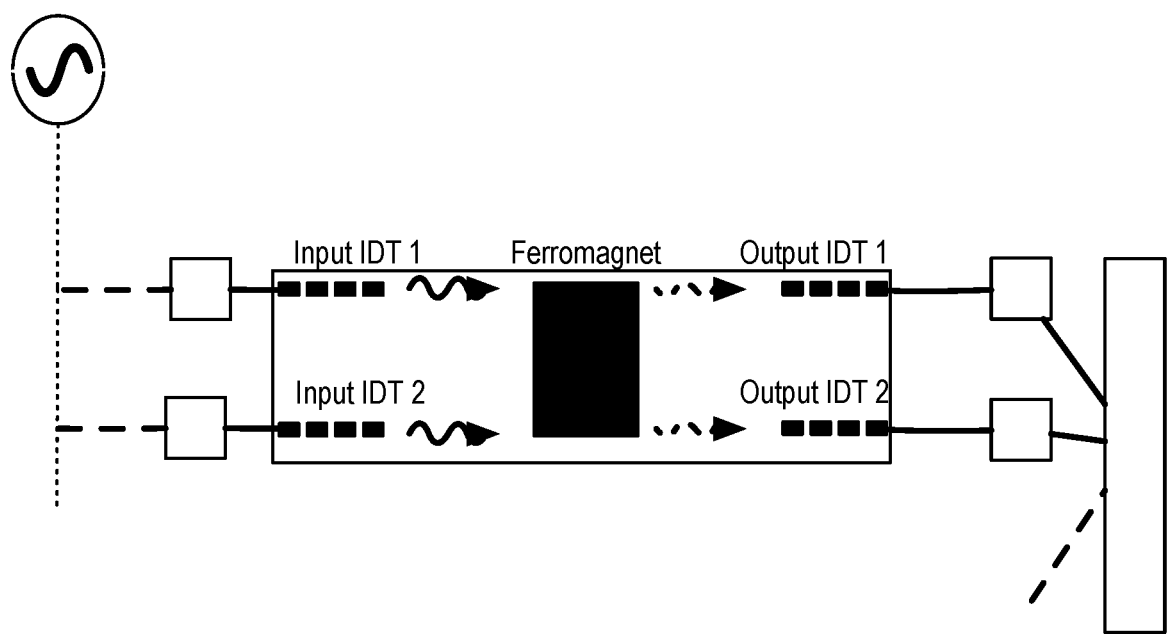
Figure 27:
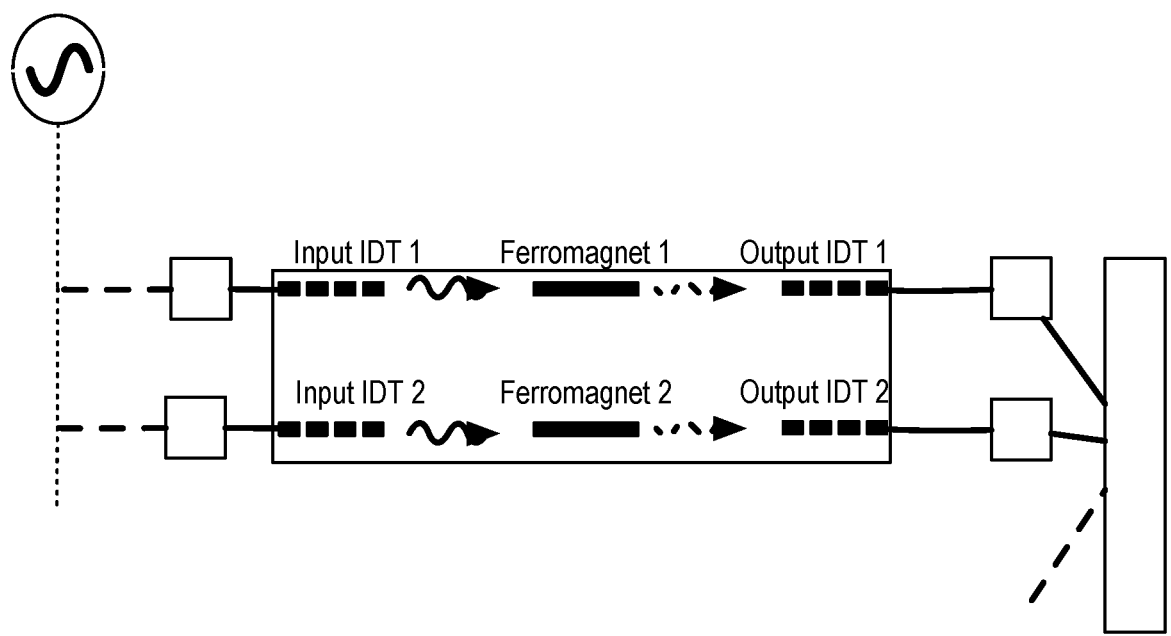
Figure 28:
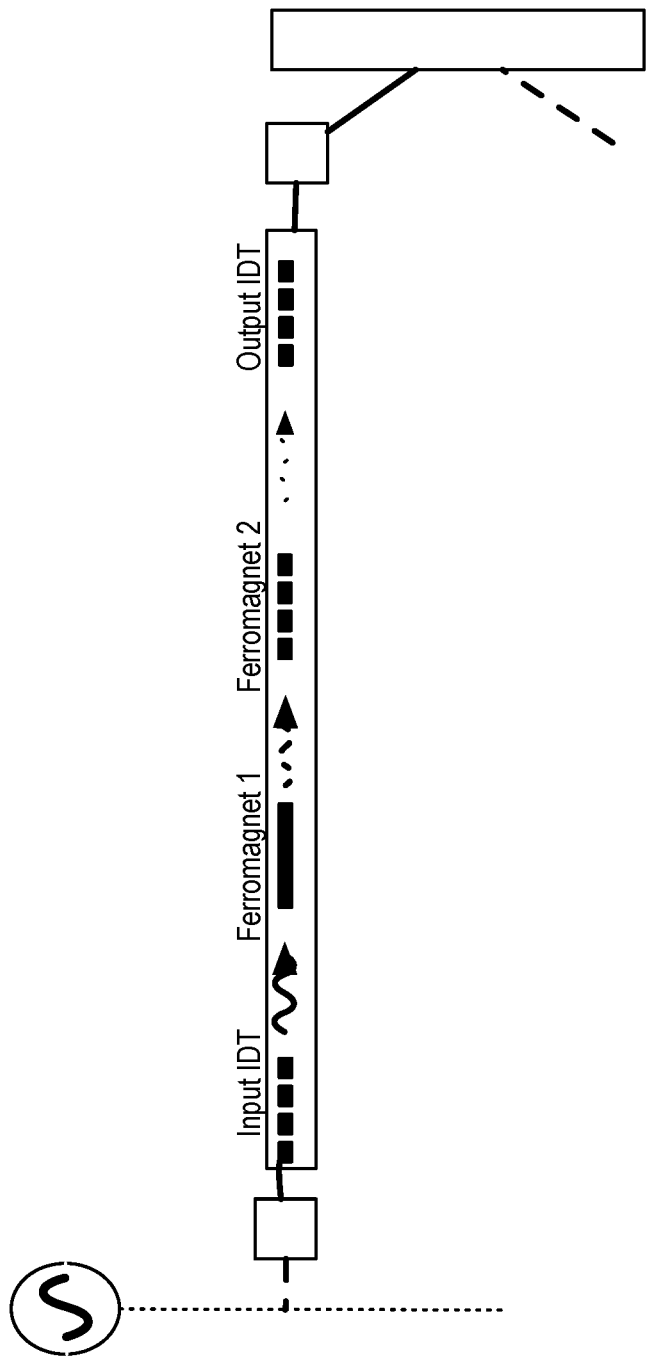

In some variations, as shown in the example FIG. 23, the ADFMR device 222 may be a SAW device. That is, in one SAW device example, the ADFMR device 222 may comprise: two IDTs, an input IDT and an output IDT; positioned along a piezoelectric substrate; wherein a magnetic film is positioned along the piezoelectric substrate in between the two IDTs. The specific configuration and shape of the SAW device may vary dependent on implementation. Example variations include: having a single SAW device per ADFMR circuit 120 (e.g. the FIG. 23 SAW device); having spatially oriented ferromagnets (one or more) on the SAW device, for a multidimensional field sensor, as shown in FIG. 24 and FIG. 25; utilizing a single SAW device with a single ferromagnet between multiple ADFMR circuits 120, as shown in FIG. 26; utilizing a single SAW device with multiple ferromagnets, either as an interferometer or gradiometer implementation, as shown in FIG. 27; having multiple distinctly oriented ferromagnets in series (e.g. as part of a serial multi-dimensional sensor), as shown in FIG. 28. Specific variations may include fewer, or additional components, as desired or necessary.

In some variations, the ADFMR device 222 includes a field coil (FC). The field coil could be a direct current (DC) coil and/or any suitable coil or system for creating a magnetic field. Any other suitable component that can create a field to offset the power output may be used. The field coil functions to generate a magnetic field bias to positively or negatively offset the output of the ADFMR device 222. In one variation, the field coil reduces the power output by inducing a reduced external field that the ADFMR device 222 is exposed to. The field coil may be implemented to offset the power output to a small output regime wherein circuit components function linearly, thereby reducing systematic error to non-linearities. For example, an amplifier may have a much smaller range of linear amplification as compared to the ADFMR device 222 output. Reducing the range of the sensor output would thus enable linear functionality of the amplifier. The field coil could potentially apply a magnetic field at any frequency (or combination of frequencies) as needed. For example, if the system were exposed to a large unwanted signal from power lines (e.g. 60 Hz) in addition to the Earth's field, the unwanted power line alternating field as well as the Earth's field could be cancelled out. The field coil may be used to apply any suitable type of canceling magnetic field.

The field coil may offset the power output to any desired range. In some variations, the field coil may offset the external field to near zero. In other variations, the field coil may alternatively, or additionally, offset the magnetic field to a range where the ADFMR sensor functions optimally. For example, in implementations where the system is used as a gradiometer, the field coil may offset the magnetic field to the regime where a change in the external field would lead to the largest change in power output (e.g. inflection point of the output power spectra).

The system may include a detector circuit. The detector circuit functions to take the output of the ADFMR circuits 220 (i.e. the potentially perturbed electrical signal), and any other components, and determine the EM field strength. In many variations the detector circuit comprises an analog to digital converter (ADC). An ADC functions to convert an analog signal to a digital signal. In some variations, the ADC may be utilized to convert the output signal to a digital signal for analysis. In some variations, ADCs may be implemented for each circuit (including the ADFMR circuit 120). In these variations the ADC converts the signal output of the circuit into a digital output prior to combining the circuit signals. All circuit digital outputs may then be combined to a digital output signal.

In variations that include parallel circuits, the system may additionally include power splitters 232 and/or power combiners 234. The power splitter 232 functions to split the power signal into multiple parts, enabling the connection of an additional parallel circuit component; and the power combiner 234 functions to combine multiple circuits. In many variations, the power splitter 232 enables splitting the original power signal into a test signal and a reference signal. Additionally, or alternatively, the power splitter 232 may split the power signal into multiple test signals and/or multiple reference signals. In addition to other properties, the power splitter/combiner set enables the functionality of an interferometer for field measurement. That is, a power signal may be split into two parts (e.g. test and reference signal), wherein one (or both) signals may be altered (e.g. through power absorption of a field through the ADFMR device). The field may then be measured by examining the interference pattern generated once the two signals are combined. The system may include a pair of power splitter/ combiners for each parallel circuit included in the system. Alternatively, the system may include more, or fewer, power splitter/combiner pairs for each parallel circuit included in the system. In some variations, the system may include an unequal number of power splitters 232 and power combiners 134 (e.g. one split power signal may be connected to a ground and not require a power combiner).

For some multi-dimensional implementations field detection, the system may include additional power splitters/combiners to enable the addition of ADFMR circuits 220. For example, for an implementation enabling measurement of fields in a plane, the system may include a power splitter 232 that splits the circuit into a first test circuit and a second test circuit; and a power combiner 234 that combines the first ADFMR circuit 220, that measures the field in an "x-direction", and a second ADFMR circuit, that measures the field in a "y-direction". The system may additionally have a second pair of power splitters/combiners (instead of the shown couplers), wherein the power signal is initially split into a reference signal and a test signal. Alternatively, a single test circuit may have multiple ADFMR devices 222 in series (e.g. with different orientations), such that their orientation enables measurement of the field in multiple dimensions. In some variations, these ADFMR sensors in series may function simultaneously, wherein other variations they may alternate.

As discussed previously, the system may additionally include a combination of various subcomponents. Example subcomponents include: signal amplifiers, bandpass filters, attenuators, inductors, phase shifters, couplers, mixers, matching networks, field coils, and comparators. Subcomponents may be incorporated on test circuits, signal processing circuits, or on any other part of the system as desired.

In some variations, the system includes at least one amplifier (A). An amplifier functions to increase the signal strength. The amplifier may help counteract the effects of power dissipation and reduced power due to splitting the original power. The amplifier may be an active or passive amplifier.

In some variations, the system may include attenuators (l). An attenuator functions to reduce the power of the signal without affecting the signal waveform. In some variations, attenuators are implemented to reduce noise. Additionally, the attenuators may match the power signal amplitude between parallel circuits (e.g. between a test circuit and a reference circuit). Attenuators may be digital or analog. In some variations digital attenuators are used to maximize removal of 1/f "pink" noise; noise proportional to the power. Analog attenuators also reduce 1/f noise, but are dependent on the noise signal of their control voltage. In some variations, the ADFMR circuit 120 may include an attenuator.

In some variations, the system includes at least one bandpass filter (F). A bandpass filter functions by narrowing the electrical signal band, thereby enabling a narrower wave band for application and/or analysis. This may additionally be the case once a signal is amplified which may naturally broaden signal spectrum.

In some variations, the system includes at least one inductor (L). An inductor functions to store energy in a magnetic field. Matching inductors may match the impedance of the transducer to any circuit component adjacent to the transducer. In some variations, the system may include matching inductors that match acoustic transducers to mixer input.

In some variations, the system includes at least one phase shifter ($\gamma$). The phase shifter function by "shifting" the phase of the electrical signal. The phase shifter may be implemented to apply constructive or destructive interference between parallel circuits that are then combined. This is particularly important in implementing an interferometer.

In some variations, the system may include at least one mixer (i.e. frequency mixer (X)). The mixer functions to combine two electrical signals into one. The mixer may multiply signals enabling frequency mixing. In some variations, the mixer may bring down a ~1 Ghz frequency from the ADFMR device 222 to a 0 frequency DC. Additionally, the mixer may enable mixing the original power source 110 signal with the ADFMR device 222 output to remove electronic oscillator noise.

In some variations, the system includes at least one coupler. A coupler functions by coupling power travelling through one circuit to another circuit, enabling the same signal to be used in another circuit. In some variations the coupler may be used instead of a power splitter to maintain the same level of power in both paths. In some variations, the system may additionally include a hybrid coupler. The hybrid coupler enables coupling two input sources to two output sources. In some preferred variations, the hybrid coupler is implemented two split a single input source and shift the phase of the output sources.

In some variations, the system includes at least one matching network. The matching network may comprise a combination of inductors and capacitors. The matching network may function to both make an impedance match between the acoustic transducer and adjacent circuit components (e.g. mixer input) and allow the transducer impedance to appear high such that it can be attached to a high-efficiency (low power) oscillator. In some variations, matching networks may match the impedance of the transducer to any circuit component adjacent to the transducer. In some variations, the system may include matching networks that match acoustic transducers to mixer input.

In some variations, the system includes at least one comparator ($\geq$). The comparator functions to detect the sign of the output signal, i.e. positive, negative, or zero. The comparator may be used with a logic circuit, to enable incremental changes to the output signal.

As mentioned previously, the system includes at least one ADFMR circuit 220 (i.e. a first ADFMR circuit), comprising, at least, one ADFMR device 222; wherein each ADFMR circuit includes an ADFMR device subcomponent and/or shares an ADFMR device subcomponent with other ADFMR circuits The ADFMR circuit 220 functions to measure the external magnetic field. Dependent on variation, each ADFMR circuit 220 may be identical or distinct. The ADFMR circuit 220 may have additional subcomponents depending on implementation. For example, in one implementation, the ADFMR circuit 220 may include matching networks. In other variations, the ADFMR circuit 220 may include inductors and/or attenuators. The ADFMR circuit 220 may additionally or alternatively have other components, such as an amplifier or a phase shifter.

In one "low-power" variations the ADFMR circuit 220 includes a matching network. In this variation, the matching network may function to match the impedance of the ADFMR circuit with another circuit. In this variation, the system may include a high-impedance power source (e.g. oscillator), and the acoustic transducers of the ADFMR device may be lower-impedance.

Figure 14:
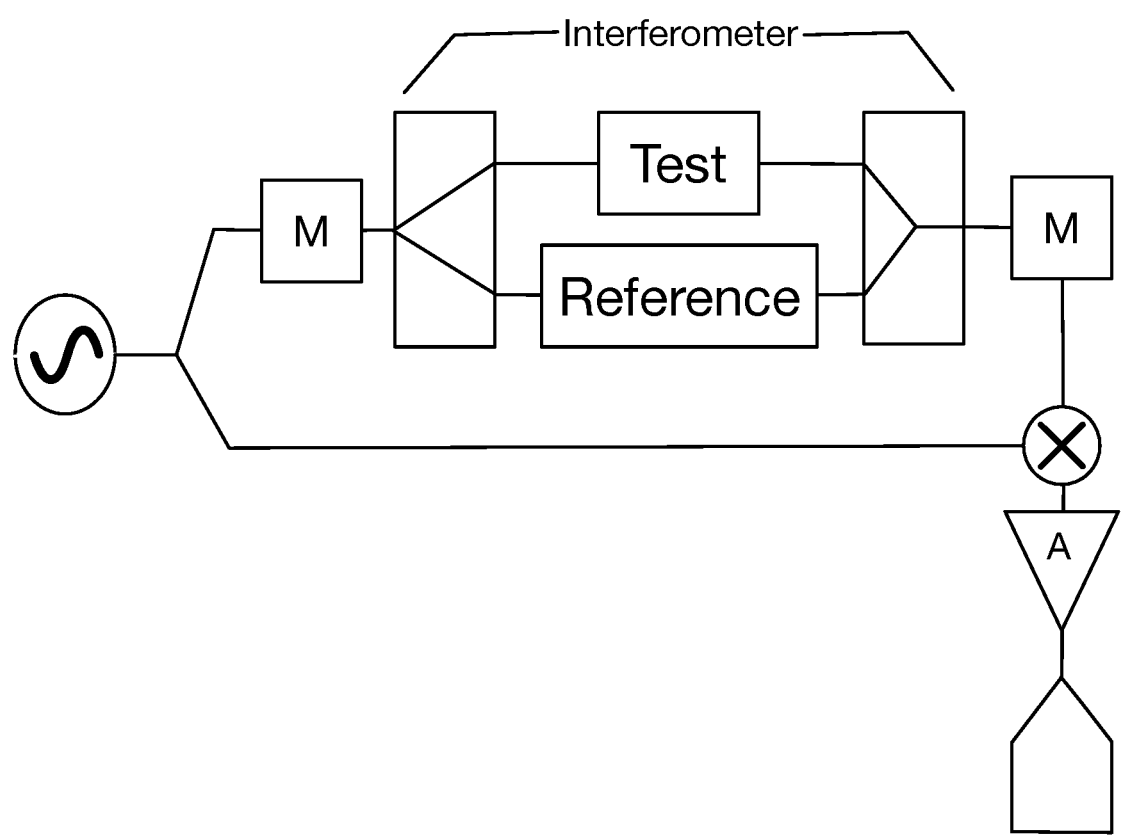
FIG. 14 is a schematic representation of a low energy interferometer ADFMR sensor.

In one lower power example, as shown in FIG. 14, the ADFMR sensor may include only a mixer and a detection circuit. The low power example functions in detecting fields at very low power consumption (less than 25 µW). In variations wherein the ADFMR device comprises a SAW device, the system may additionally include a matching network prior to the interferometer and after the interferometer. The matching network may provide high resistance and match the IDT impedance to the electronic oscillator and mixer impedance, thereby matching their voltages.

Figure 15:
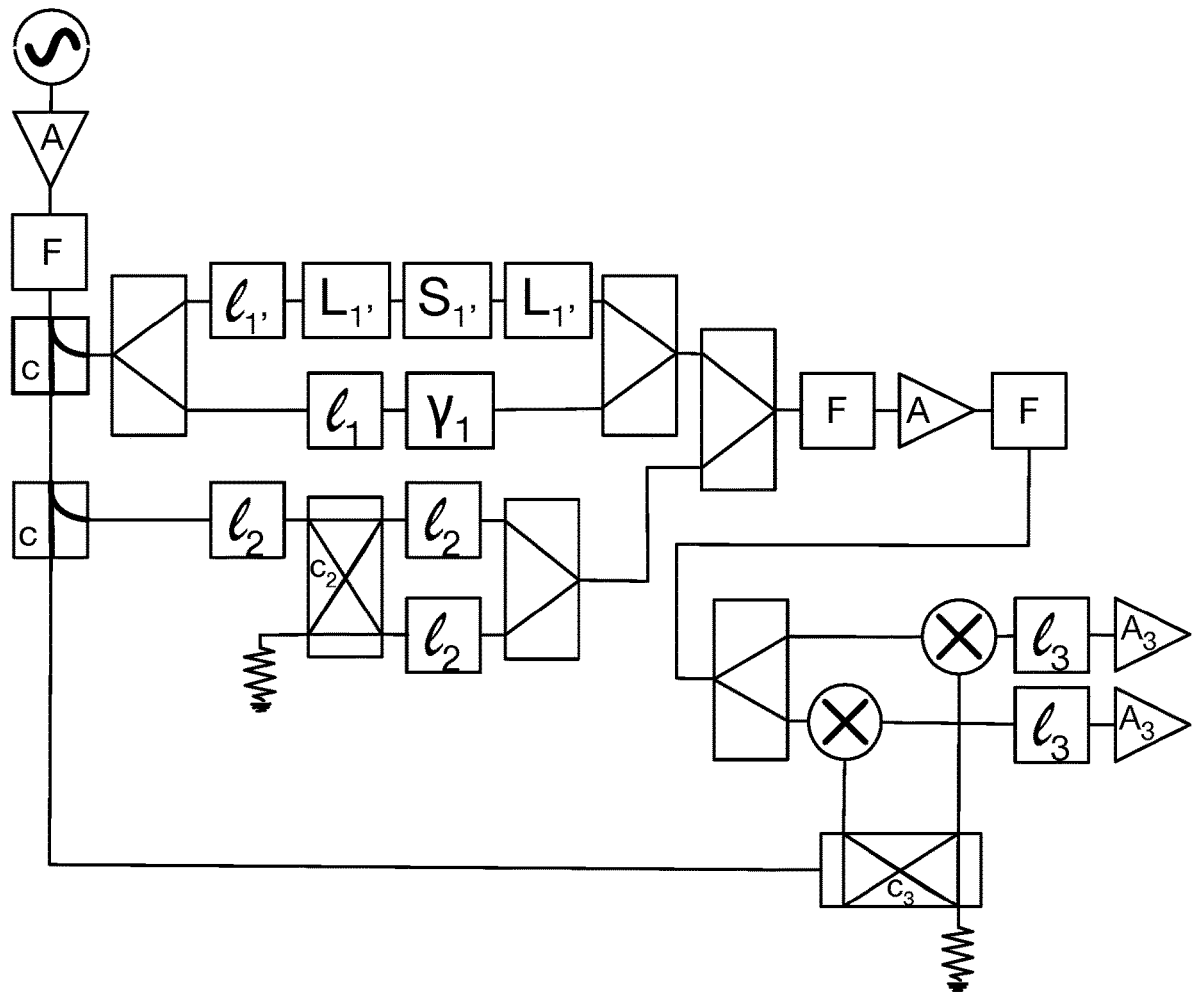
FIG. 15 is a schematic representation of an interferometer ADFMR sensor that implements noise reduction.

In one general interferometer application example, as shown in FIG. 15, the interferometer additionally includes a vector modulator circuit, an IQ mixer circuit, an amplification circuit, and a detection circuit. In this example, the amplification circuit amplifies the output of the "inner" interferometer and an "outer" interferometer, vector modulator circuit, which then connect to an IQ mixer circuit. All signals eventually combine and are output to the detection circuit. The general application example functions to measure fields as desired. This example may be additionally or alternatively implemented for a gradiometer system.

Figure 16:
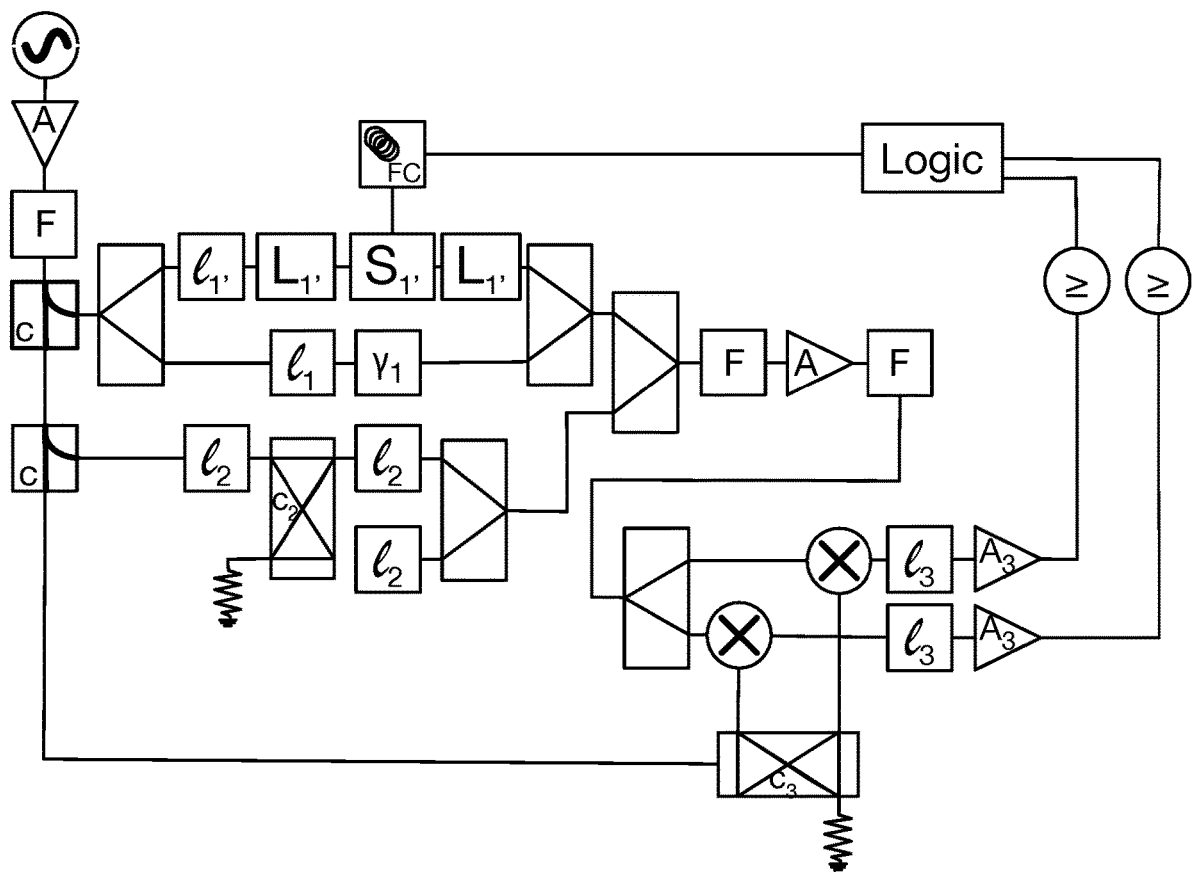
FIG. 16 is a schematic representation of a large disparity EM field interferometer.

In one large disparity example, as shown in FIG. 16, that may include large disparity in field strengths, the general application example may additionally include a linearization circuit. The large disparity example functions to precisely measure fields that may have a large disparity in magnitude. Although the general application example could function over a wide range, the large disparity example includes a feedback loop that may reduce non-linear effects due to the wide disparity of field magnitudes, thereby making field measurements more accurate.

4. Method

As shown in FIG. 29, a method for measuring EM field biological activity through a wearable field-measuring device comprising: enabling the field-measuring device S110, wherein the field-measuring device comprises a device capable of measuring EM fields in tissue adjacent to the device; monitoring device sensors in desired measuring regions S120; and localizing field activity S130, comprising identifying the source of the EM field activity and removing noise. The method functions to identify the source of biological activity and monitor the biological activity through the measurement of EM fields of a living organism (e.g. human) proximal to the region of activity. The method preferably functions with a wearable field-measuring device, preferably a device similar to the one described above.

The method may be implemented with different wearable devices to observe different types of biological activity. For example, a helmet, or portable cap, device may monitor brain activity; leg bands and other body bands may be utilized to monitor muscle activity; and a chest band or chest patch may be utilized to monitor heart activity. The method is preferably implemented by a system or variation thereof of the system described above. However, any suitable system may alternatively be used.

The field-measuring device may be a "wearable" form factor, housing for sensors dispersed densely on the interior region of the form factor. The field-measuring device may have any desired general form, but will, generally speaking, have an "interior" shape to match the contours of the wearer, particularly the region of desired field measurement. Examples of the general shape of the field-measuring device include: helmet, headband, wristband, leg-band, girdle, and form fitting patch.

Preferably, sensors are densely dispersed on the interior of the field-measuring device. Generally speaking, the field-measuring device may have a 1-10000 sensors in a desired implementation, wherein the method enables a large variability of implementations. Dependent on the size of the desired region of measurement, and other factors, field-measuring device may have a fewer or a greater number of sensors. In preferred variations, the sensors are ADFMR sensors, as described in other regions, but may alternatively be any sensor device that is sufficiently compact, as described, and sufficiently sensitive to measure biological EM fields from the surface skin of an individual.

Block S110, which includes enabling the field-measuring device, functions to enable sensor activation. Enabling the field-measuring device S110 includes setting the device such that the device sits firmly in place with sensors adjacent to the skin of an individual (or adjacent to surface of another object to be monitored) over a desired region of measurement. In this manner, enabling the field-measuring device S110 may include wearing the device. To be noted, the term "wearing" here is used to refer to fixing the field-measuring device in place on the body of the user. Wearing thus may include wearing a hat by fixing it around the crown of the head of a person, adhering a patch to the chest of the user, stretching a band around a leg of the user, or any other action that fixes the field-measuring device in place appropriately. Wearing of the device can additionally enable the device to move with the user. As a wearable device, the sensors preferably stay substantially stationary relative to the user thereby measuring the same location even when the user moves. This can be particularly useful over other MEG systems that can be sensitive to user movement greater than 0.5 cm especially when measuring physical activities, children, animals, and the like.

Enabling the field-measuring device S110 preferably includes wearing the device such that the sensors are in sufficient proximity with a wearer. In preferred variations, the distance between the sensors and the user skin is less than 1 cm.

Enabling the field-measuring device S110, preferably includes different actions dependent on implementations, or combinations of implementations. In one implementation, the field-measuring device is specifically built to fit the contour of a user (e.g. a helmet) and enabling the field-measuring device S110 includes placing the field-measuring device in place. In a second implementation, the field-measuring device may be composed of stretchable material (e.g. leg band) and enabling the field-measuring device S110 includes stretching the device over the desired region. In a third implementation, the field-measuring device may be malleable, or semi-malleable (e.g. soft metals such as aluminum), and enabling the field-measuring device S110 includes shaping the field-measuring device around the user; e.g. an aluminum helmet. In a forth implementation, the field-measuring device may comprise of modular subcomponents, wherein enabling the field-measuring device S110 includes building the field-measuring device around the contour of the user. In a fifth implementation, the field-measuring device may comprise a patch (e.g. chest patch) and enabling the field-measuring device S110 includes adhering the patch to the chest of the user.

Block S120, which includes monitoring device sensors in a desired measuring region, functions to measure the EM field at the sensors on the field-measuring device. Depending on the implementation, block S120 may include monitoring all sensors simultaneously and/or monitoring sensors in clusters. Monitoring may occur continuously, or may occur at fixed intervals. In preferred variations S120, both the number of sensors monitoring at one time and the rate of monitoring may be altered as desired. For example, block S120 may slow the rate of brain monitoring if the time evolution of the variation in brain EM fields slows down (e.g. if a user falls asleep during observation).

In some preferred variations, block S120 includes reducing cross-talk. Reducing cross-talk preferably functions to reduce sensor noise. Reducing cross-talk comprises staggering measurement of the EM field over the sensors of the EM-field device. That is, block S120 includes monitoring spatially grouped sensors together, while turning off sensors around the spatially grouped sensors. In this manner, reducing cross-talk may reduce the sensor noise by significantly reducing noise outside of the active monitoring group of sensors.

Block S120 may also change with continuous monitoring through implementation of block S130. For example, if the main source of the EM field is determined, monitoring device sensors in a desired region S120 may narrow the desired region and only monitors sensors in proximity of the EM field source.

Block S130, which includes localizing field activity, preferably functions to identify the source of the biological EM field. In preferred variations, block S130 includes processing sensor data accrued from block S120, locating the source tissue(s) that generated the field activity, and following the time evolution of the source tissue. Generally speaking, localizing field activity S130 includes solving the inverse problem from the sensor field data.

Solving the inverse problem preferably includes solving an eigenvalue problem using numerical methods (e.g. spectral methods, least squares, Monte-Carlo simulations). In some variations, the problem may be numerically too intensive to arrive at a solution with sufficient accuracy in a reasonable amount of time. This may be due to the number of sensor field points, system and external noise, and the rate of the time evolution of the EM field(s). In these variations, block S130 preferably includes optimization techniques to improve both the speed and accuracy of solving the inverse problem.

In some preferred variations, block S130 includes spatially averaging sensor data. Spatially averaging sensor data preferably functions to reduce the complexity of the inverse problem and to reduce system noise by averaging sensor data into local clusters. Spatially averaging sensor data enables solving the inverse problem over a smaller set sensor points, thereby reducing the processing time of the calculation at the cost of reduced precision. Dependent on the complexity of the problem and the method implementation, the magnitude of the spatial averaging may be different for any given implementation. Additionally, as the monitored system evolves, the use of other optimization techniques (e.g. recursive techniques, improved starting value guesses) may be implemented to reduce magnitude of spatial averaging. For example, in some variations, or during certain times of activity, coarse location determination may be implemented in addition, or as an alternative, to spatial averaging sensor data. Coarse location determination may include utilizing a sparse selection of sensors (e.g. utilizing 1 of every 100 sensors).

In some variations, the method may additionally incorporate other processes for enhancing sensing and/or characterizing activity.

As one exemplary variation, the method may additionally include sensing device orientation and correcting sensor data for a stationary magnetic field. This can function to remove the earth's magnetic field and/or other magnetic field sources from the data. Sensing device orientation when the system is a head-worn device can include sensing head position and/or orientation. In one implementation sensing head orientation can include sensing with a magnetic sensor (e.g., a magnetometer) the earth's magnetic field and subtracting this field from sensor data of preferably all sensors. This subtraction can account for relative orientation and position of each sensor relative to the magnetic sensor. Since the noise is shared among all ADFMR sensors, it may be removable with synthetic gradiometry or any suitable alternative process. Sensing head orientation may be used for determining individual sensor orientation relative to the magnetic field. An IMU, accelerometer, cameras (on the device using inside out visual tracking or off device using outside-in visual tracking), and/or any suitable tracking system may be used. Motion tracking of the head may be continuously updated such that noise removal can be continuously updated.

Other forms of noise removal may additionally or alternatively be used. In some use cases, the method may include detecting and/or characterizing a background noise profile and synthetically removing the background noise. These external sources of noise may be from other electronic devices present in the environment. As one exemplary approach, the method may include: initiating a calibration mode where a background noise profile is generated, detecting frequency ranges where the noise is present based on the background noise profile, and filtering out the identified frequency ranges of the noise from the sensor data. In some cases, select frequency ranges may be filtered out by default.

In some alternative implementations noise may be addressed through physical design and configuration of the system such as by orienting sensors to be minimally sensitive to magnetic fields generated by other electronics, and/or by shielding magnetic sensors from other electronics using special electrical control signals or optical connections as discussed herein.

In another variation, the method may include processes to accommodate interference from other human activity. This may be used to isolate sensed and/or detected activity from other signal activity. Such variations may further include sensing human activity and removing induced bio-signal noise from the sensor data. This can include using additional biometric sensors, motion sensors, or external tracking sensors (e.g., external imaging systems) to detect and track actions. In one variation, the detected activity is motion information of the user. For example, the method may include collecting image data of a user; detecting blinks, arm movements, finger movements, talking, and/or other muscle movements from the visual data; and applying a filter process on the sensor data to reduce or remove signal contributions from this activity.

As another variation, the method may include contextually activating system. This functions to dynamical adjust the activation of different subsets of sensors to accommodate the current conditions. Here activating (and/or deactivating) may describe any suitable change in the sensing modes. In one example, activating may include powering on a sensor and deactivating includes powering off. Activating may also include changing other operating properties such as changing power mode, changing sampling frequency, changing sensing range, and/or making other changes to the sensing.

In one variation, the monitoring state of the device can be dynamically altered based on the state of a connected device. This can include detecting the operating mode of a connected device and altering the sensing mode, e.g. as part of a brain computer interface (BCI) interaction. As a first example, if a user is moving a character in a video game, then this motion activity may be used to trigger activating a motor cortex sensing region. As another example, if a computing device is measuring reactions to visual stimuli, then this may trigger activating a visual cortex sensing region and deactivating other regions. This may be particularly applicable to simulators (e.g. a flight simulator).

In another related variation, the method can include monitoring multiple sensing regions, detecting an activity state, and, in response to one activity state, isolating sensing to one or more sensing region. This may enable the method to adaptively alter monitoring mode based on the current activity. This may be particularly useful in open-scenario situations where there may be no information or limited information on the current task. Monitoring multiple sensing regions may be performed in a low power mode until localized sensing is triggered from some event.

Dynamic isolated monitoring may localize sensing to multiple mental functions or activities. For example, a low power background activity monitoring may detect engagement with motor-based and visual-based activity and then activate sensing localized to the motor cortex sensing region or the visual cortex sensing region.

The configuration of localized sensing may be learned. Configuration of sensing for different activity modes may be learned according to patterns in sensed data from one or more users. In one implementation, machine learning or other algorithmic approaches may be trained to determine which tasks are commonly associated with each other (e.g., commonly paired or follow each-other), this may be used to adjust the sensing based on predictive expectations. The configuration of localized sensing for different activity modes may alternatively be fully or partially preconfigured. The preconfiguration may be set based on knowledge of the brain (e.g., which regions correspond to what activity), and/or set based on prior analysis of activities.

4. System Architecture

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

In one variation, a system comprising of one or more computer-readable mediums storing instructions that, when executed by the one or more computer processors, cause a computing platform to perform operations comprising those of the system or method described herein such as: enabling a field measuring device; monitoring device sensors in desired measuring regions; localizing field activity.

Similarly, in another variation, a non-transitory computer-readable medium storing instructions that, when executed by one or more computer processors of a communication platform, cause the communication platform to perform operations of the system or method described herein such as: monitoring device sensors in desired measuring regions; localizing field activity.

Figure 30:
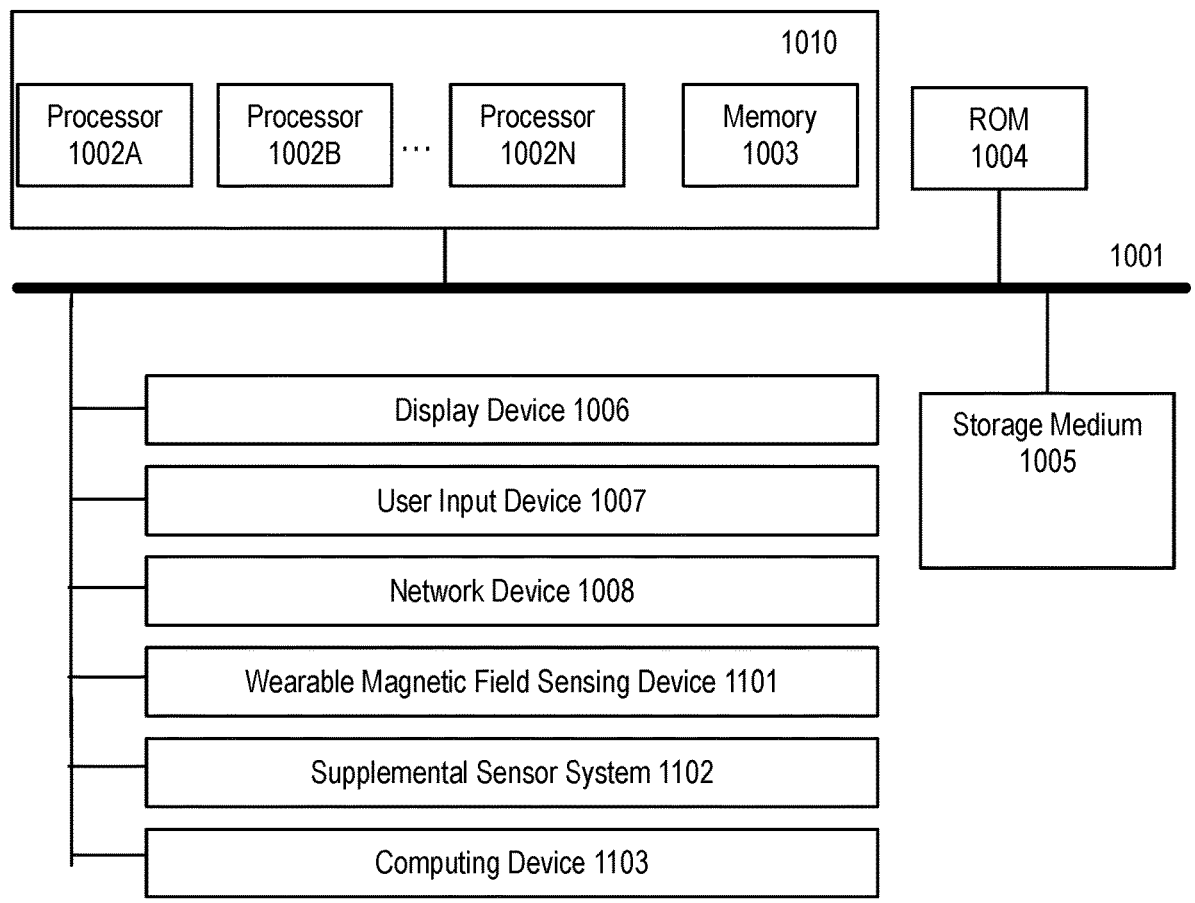
FIG. 30 is an exemplary system architecture that may be used in implementing the system and/or method.

FIG. 30 is an exemplary computer architecture diagram of one implementation of the system. In some implementations, the system is implemented in a plurality of devices in communication over a communication channel and/or network. In some implementations, the elements of the system are implemented in separate computing devices. In some implementations, two or more of the system elements are implemented in same devices. The system and portions of the system may be integrated into a computing device or system that can serve as or within the system.

The communication channel 1001 interfaces with the processors 1002A-1002N, the memory (e.g., a random access memory (RAM)) 1003, a read only memory (ROM) 1004, a processor-readable storage medium 1005, a display device 1006, a user input device 1007, and a network device 1008. As shown, the computer infrastructure may be used in connecting wearable field sensing device 1101, biological sensor array 1102, control circuitry 1103 and/or other suitable computing devices.

The processors 1002A-1002N may take many forms, such CPUs (Central Processing Units), GPUs (Graphical Processing Units), microprocessors, ML/DL (Machine Learning/Deep Learning) processing units such as a Tensor Processing Unit, FPGA (Field Programmable Gate Arrays, custom processors, and/or any suitable type of processor.

The processors 1002A-1002N and the main memory 1003 (or some sub-combination) can form a processing unit 1010. In some embodiments, the processing unit includes one or more processors communicatively coupled to one or more of a RAM, ROM, and machine-readable storage medium; the one or more processors of the processing unit receive instructions stored by the one or more of a RAM, ROM, and machine-readable storage medium via a bus; and the one or more processors execute the received instructions. In some embodiments, the processing unit is an ASIC (Application-Specific Integrated Circuit). In some embodiments, the processing unit is a SoC (System-on-Chip). In some embodiments, the processing unit includes one or more of the elements of the system.

A network device 1008 may provide one or more wired or wireless interfaces for exchanging data and commands between the system and/or other devices, such as devices of external systems. Such wired and wireless interfaces include, for example, a universal serial bus (USB) interface, Bluetooth interface, Wi-Fi interface, Ethernet interface, near field communication (NFC) interface, and the like.

Computer and/or Machine-readable executable instructions comprising of configuration for software programs (such as an operating system, application programs, and device drivers) can be stored in the memory 1003 from the processor-readable storage medium 1005, the ROM 1004 or any other data storage system.

When executed by one or more computer processors, the respective machine-executable instructions may be accessed by at least one of processors 1002A-1002N (of a processing unit 1010) via the communication channel 1001, and then executed by at least one of processors 1001A-1001N. Data, databases, data records or other stored forms data created or used by the software programs can also be stored in the memory 1003, and such data is accessed by at least one of processors 1002A-1002N during execution of the machine-executable instructions of the software programs.

The processor-readable storage medium 1005 is one of (or a combination of two or more of) a hard drive, a flash drive, a DVD, a CD, an optical disk, a floppy disk, a flash storage, a solid state drive, a ROM, an EEPROM, an electronic circuit, a semiconductor memory device, and the like. The processor-readable storage medium 1005 can include an operating system, software programs, device drivers, and/or other suitable sub-systems or software.

As used herein, first, second, third, etc. are used to characterize and distinguish various elements, components, regions, layers and/or sections. These elements, components, regions, layers and/or sections should not be limited by these terms. Use of numerical terms may be used to distinguish one element, component, region, layer and/or section from another element, component, region, layer and/or section. Use of such numerical terms does not imply a sequence or order unless clearly indicated by the context. Such numerical references may be used interchangeable without departing from the teaching of the embodiments and variations herein.

As a person skilled in the art will recognize from the previous detailed description and from the figures and claims, modifications and changes can be made to the embodiments of the invention without departing from the scope of this invention as defined in the following claims.

We claim:

1. A system for a wearable field sensing device for biological electromagnetic (EM) field measurement comprising:
   a wearable structure, comprising a portable cap fitted to a user head;
   a biological sensor array,
      situated on the portable cap such that a plurality of sensors in the biological sensor array is adjacent to the user head once the portable cap is worn,
      spans at least one distinct region of the user head, for field measurements in the at least one distinct region,
      the biological sensor array comprising an array of acoustically driven ferromagnetic resonance (ADFMR) sensor units situated on the interior of the wearable structure, an ADFMR sensor unit being an application specific integrated circuit (ASIC) package that comprises at least one ADFMR sensor, excitation circuitry connected as a frequency source to the at least one ADFMR sensor, and ADMR signal processing circuitry,
      the biological sensor array comprises at least 100 ADFMR sensors in the at least one distinct region, and
   an ambient sensor array, comprising:
      a second array of ADFMR sensor units situated on the portable cap configured to measure ambient EM fields in proximity of the portable cap;
   sensor shielding, comprising a set of field coils situated on the portable cap and enabled to generate magnetic fields on and around the portable cap;
   a power system, comprising a battery electrically coupled to the portable cap; and
   control circuitry, electrically coupled to the system,
      enabling the system to function in a low power operating mode, comprising operation of a subset of the biological sensor array, and
      enabling the system to function in a noise reduction operating mode, wherein the noise reduction operating mode comprises activating the set of field coils to cancel ambient EM fields measured by the ambient sensor array.

2. A system for a wearable field sensing device for biological electromagnetic (EM) field measurement comprising:
   a wearable structure;
   a biological sensor array, comprising an array of acoustically driven ferromagnetic resonance (ADFMR) sensor units situated on an interior of the wearable structure, an ADFMR sensor unit being an application specific integrated circuit (ASIC) package that comprises at least one ADFMR sensor, excitation circuitry connected as a frequency source to the at least one ADFMR sensor, and ADMR signal processing circuitry;
   a power system, comprising an energy source for the system; and
   control circuitry, conductively coupled to the biological sensor array.

3. The system of claim 2, wherein the wearable structure comprises a patch, wherein the patch is shaped to, at least, partially cover a user body region for EM field measurement.

4. The system of claim 2, wherein the wearable structure comprises a cap shaped to, at least, partially cover a head region of a user for EM field measurement.

5. The system of claim 4, wherein the cap comprises a deformable cap such that the deformable cap may sufficiently change in size and shape to fit the head region of the user, wherein the deformable cap comprises deformable regions that may change in size and shape and rigid regions that do not change in size and shape.

6. The system of claim 5, wherein the biological sensor array is situated on the rigid regions of the deformable cap.

7. The system of claim 2, wherein the biological sensor array comprises 1-10 ADFMR sensors.

8. The system of claim 2, wherein the biological sensor array comprises 10-100 ADFMR sensors.

9. The system of claim 2, wherein the biological sensor array comprises 100-1000 ADFMR sensors.

10. The system of claim 2, wherein the biological sensor array comprises 1,000-10,000 ADFMR sensors.

11. The system of claim 2, wherein the biological sensor array comprises 10,000-100,000 ADFMR sensors.

12. The system of claim 2, wherein the biological sensor array comprises at least 100,000 ADFMR sensors.

13. The system of claim 2, further comprising an ambient sensor array, wherein the ambient sensor array is electrically coupled to the control circuitry and is configured to measure ambient EM fields in proximity of the wearable structure.

14. The system of claim 13, wherein at least a subset of the ambient sensor array sensors comprises ADFMR sensors.

15. The system of claim 13, wherein at least a subset of the ambient sensor array sensors comprises magnetometers.

16. The system of claim 13, further comprising sensor shielding, wherein the sensor shielding comprises electrical coils configured to generate a magnetic field to counteract the measured ambient EM fields.

17. The system, of claim 2, further comprising sensor shielding, wherein the sensor shielding comprises a mu-metal covering over the biological sensor array.

18. The system of claim 2, wherein the system, through the control circuitry, is enabled to function in a low power mode, wherein only a subset of the sensors from the biological sensor array are active until biological activity is detected.

19. The system of claim 18, wherein the biological sensor array comprises at least one biosensor; wherein the biological activity is detected based on a signal from the at least one biosensor.

20. The system of claim 2, wherein the ADFMR sensor unit further comprises a second ADFMR sensor, and the ADFMR signal processing circuitry integrates the second ADFMR sensor with the at least one ADFMR sensor as a gradiometer.

* * * * *